US011717187B2

(12) United States Patent
Lim et al.

(10) Patent No.: US 11,717,187 B2
(45) Date of Patent: Aug. 8, 2023

(54) WALKING ASSISTANCE METHOD AND APPARATUSES

(71) Applicant: Samsung Electronics Co., Ltd., Suwon-si (KR)

(72) Inventors: Bokman Lim, Yongin-si (KR); Youngjin Park, Seoul (KR); Keehong Seo, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 796 days.

(21) Appl. No.: 16/164,766

(22) Filed: Oct. 18, 2018

(65) Prior Publication Data

US 2019/0046078 A1    Feb. 14, 2019

Related U.S. Application Data

(63) Continuation-in-part of application No. 15/861,832, filed on Jan. 4, 2018, now Pat. No. 11,109,778.

(30) Foreign Application Priority Data

Jun. 15, 2017    (KR) .................. 10-2017-0075634

(51) Int. Cl.
*A61B 5/11* (2006.01)
*B25J 9/00* (2006.01)
(Continued)

(52) U.S. Cl.
CPC ............ *A61B 5/112* (2013.01); *A61H 1/0237* (2013.01); *A61H 3/00* (2013.01); *B25J 9/0006* (2013.01);
(Continued)

(58) Field of Classification Search
CPC ............ A61H 2230/60; A61H 2230/08; A61H 2230/0406; A61H 2205/10;
(Continued)

(56) References Cited

U.S. PATENT DOCUMENTS 9,308,642 B2 * 4/2016 Sugar .................. B25J 9/0006
10,537,733 B2    1/2020 Dixon et al.
(Continued)

FOREIGN PATENT DOCUMENTS

JP          5128375 B2    1/2013
JP     2016-002408 A     1/2016
(Continued)

OTHER PUBLICATIONS

Notice of Allowance dated Apr. 29, 2021 in corresponding U.S. Appl. No. 15/861,832.
(Continued)

*Primary Examiner* — Patrick Fernandes
(74) *Attorney, Agent, or Firm* — Harness, Dickey & Pierce, P.L.C.

(57) ABSTRACT

A walking assistance method and/or apparatuses configured to perform same are provided. A state variable may be defined based on a result obtained by measuring a gait motion of a user, and a torque profile may be generated based on the defined state variable, a gain and a delay. The generated torque profile may correspond to a torque profile to assist the gait motion, or a torque profile to provide a resistance to the gait motion.

10 Claims, 28 Drawing Sheets

(51) Int. Cl.
*A61H 3/00* (2006.01)
*A61H 1/02* (2006.01)
(52) U.S. Cl.
CPC ............... *A61H 2201/1215* (2013.01); *A61H 2201/165* (2013.01); *A61H 2201/1642* (2013.01); *A61H 2201/1652* (2013.01); *A61H 2201/501* (2013.01); *A61H 2201/5005* (2013.01); *A61H 2201/5046* (2013.01); *A61H 2201/5061* (2013.01); *A61H 2201/5069* (2013.01)
(58) Field of Classification Search
CPC .... A61H 2201/5069; A61H 2201/5061; A61H 2201/5058; A61H 2201/5046; A61H 2201/5043; A61H 2201/5007; A61H 2201/165; A61H 2201/164; A61H 2201/1628; A61H 2201/14; A61H 2201/1215; A61H 2003/007; A61H 3/008; A61H 3/00; A61H 2001/0251; A61H 2001/0248; A61H 1/0244; A61H 1/0237; A61H 2201/1642; A61H 2201/1652; A61H 2201/5005; A61H 2201/501; A61H 1/0266; A61F 2002/701; A61F 2002/6827; A61B 5/4851; A61B 5/1121; A61B 5/1116; A61B 5/112; A61B 2562/0219; A61B 2562/0252; B25J 9/00006

See application file for complete search history.

(56) References Cited

U.S. PATENT DOCUMENTS

| | | | | |
|---|---|---|---|---|
| 2009/0227925 | A1* | 9/2009 | McBean | A61F 5/0127 602/16 |
| 2012/0016278 | A1 | 1/2012 | Nakashima et al. | |
| 2015/0127018 | A1 | 5/2015 | Lim et al. | |
| 2015/0366738 | A1* | 12/2015 | Endo | A61H 3/00 482/4 |
| 2016/0143800 | A1* | 5/2016 | Hyung | A61H 3/00 623/32 |
| 2016/0331560 | A1 | 11/2016 | Tong et al. | |
| 2016/0338897 | A1 | 11/2016 | Takenaka et al. | |
| 2017/0043476 | A1 | 2/2017 | Seo et al. | |
| 2017/0340506 | A1* | 11/2017 | Zhang | A61H 1/024 |

FOREIGN PATENT DOCUMENTS

| | | | |
|---|---|---|---|
| JP | 5892506 | B2 | 3/2016 |
| JP | 2016214504 | A | 12/2016 |
| KR | 10-2016-0098354 | A | 8/2016 |
| KR | 20170016638 | A | 2/2017 |

OTHER PUBLICATIONS

C. Abdallah et al., "Delayed Positive Feedback Can Stabilize Oscillatory Systems", American Control Conference, Jun. 1993 (pp. 3106-3107), IEEE.

Rush D. Robinett et al., "Lag-Stabilized Force Feedback Damping," Journal of Intelligent and Robotic Systems, vol. 21, pp. 277-285, 1998, Copyright © 1998 Khuwer Academic Publishers.

S. G. Chen et al., "Computational Stability Analysis of Chatter in Turning", Journal of Manufacturing Science and Engineering, Nov. 1997, vol. 119, pp. 457-460, Copyright © 1997 by ASME.

P. Hövel et al., "Control of unstable steady states by time-delayed feedback methods", Dates May 30, 2005, PhysCon 2005, pp. 360-367, St. Petersburg, Russia.

Non-Final Office Action dated May 27, 2020 for U.S. Appl. No. 15/861,832.

Korean Office Action issued by Korean Intellectual Property Office (KIPO) dated Dec. 13, 2021 for the corresponding KR Patent Application No. 10-2017-0075634.

* cited by examiner

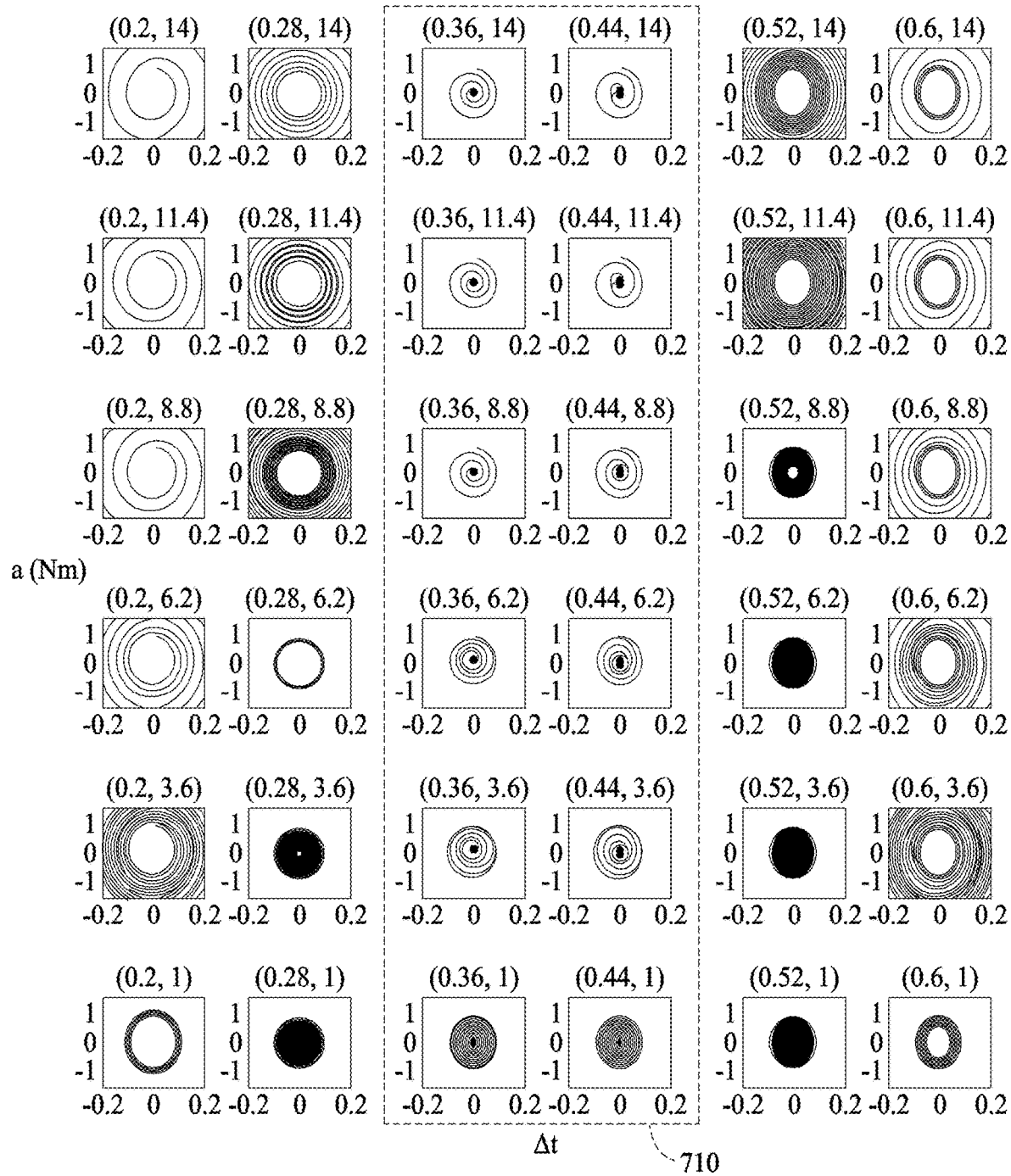

1800

WALKING ASSISTANCE METHOD AND APPARATUSES

CROSS-REFERENCE TO RELATED APPLICATION

This application is a continuation-in-part of U.S. patent application Ser. No. 15/861,832, filed on Jan. 4, 2018, and claims priority under 35 U.S.C. § 119 to Korean Patent Application No. 10-2017-0075634, filed on Jun. 15, 2017, in the Korean Intellectual Property Office, the entire contents of each of which are incorporated herein by reference in its entirety.

BACKGROUND

1. Field

At least one example embodiment relates to a walking assistance method and/or an apparatuses configured to perform same.

2. Description of the Related Art

With the onset of rapidly aging societies, an increased number of people who experience inconvenience and agony from joint problems is increasing, and accordingly an interest in motion assistance apparatuses that may enable the elderly or patients having joint problems to walk with less effort is growing. Also, motion assistance apparatuses to increase a muscular strength of a human body are being developed, for example, for military purposes.

For example, a motion assistance apparatus may include a body frame disposed on a trunk of a user, a pelvic frame coupled to a lower side of the body frame to cover a pelvis of the user, a femoral frame disposed on a thigh of the user, a sural frame disposed on a calf of the user, and a pedial frame disposed on a foot of the user. The pelvic frame and the femoral frame may be connected rotatably by a hip joint portion, and the femoral frame and the sural frame may be connected rotatably by a knee joint portion. Also, the sural frame and the pedial frame may be connected rotatably by an ankle joint portion.

The motion assistance apparatus may be controlled based on feed-forward based torque patterns at predicted gait phases, which may work well in steady state, but may cause problems in scenarios when it is difficult to predict the gait phases (e.g., when a user has a discontinuous or irregular gait pattern).

SUMMARY

Some example embodiments relate to an operating method of a walking assistance apparatus.

In some example embodiments, the operating method includes defining a state variable based on a result obtained by measuring a gait motion of a user; and generating a torque profile based on the state variable, a gain and a delay such that the torque profile assists the gait motion or resists the gait motion based on the gain.

In some example embodiments, the defining the state variable includes defining the state variable as a difference between a first function based on a first hip joint angle of the user and a second function based on a second hip joint angle.

In some example embodiments, each of the first function and the second function corresponds to a trigonometrical function In some example embodiments, the generating the torque profile includes generating the torque profile to assist the gait motion by applying a first gain and the delay to the state variable in response to the gain being the first gain, and generating the torque profile to resist the gait motion by applying a second gain and the delay to the state variable in response to the gain being the second gain.

In some example embodiments, a sign of the first gain and a sign of the second gain are different from each other.

In some example embodiments, the generating the torque profile determines a direction of a torque based on the gain.

In some example embodiments, the generating the torque profile determines an output timing of torque based on the delay.

In some example embodiments, the gait motion of the user includes a left hip joint angle and a right hip joint angle of the user.

In some example embodiments, the method further includes outputting torque based on the torque profile.

In some example embodiments, the method further includes filtering the result obtained by measuring the gait motion of the user.

In some example embodiments, the generating the torque profile includes determining an output timing of torque associated with the torque profile based on the delay and a time delay associated with the filtering.

Some example embodiments relate to an operating method of a walking assistance apparatus.

In some example embodiments, the method includes measuring a gait motion of a user; defining a state variable based on the gait motion; generating a torque profile based on the state variable, a gain and a delay associated with the state variable; and outputting torque to resist the gait motion based on the torque profile.

In some example embodiments, the defining the state variable includes defining the state variable as a difference between a first function based on a first hip joint angle of the user and a second function based on a second hip joint angle.

In some example embodiments, each of the first function and the second function corresponds to a trigonometrical function.

In some example embodiments, the generating of the torque profile includes generating a first torque profile corresponding to a first leg of the user by applying the gain and the delay to the state variable; and generating a second torque profile corresponding to a second leg of the user by changing a sign of the torque profile corresponding to the second leg.

In some example embodiments, the generating the torque profile determines a direction of torque based on the gain.

In some example embodiments, the generating the torque profile determines an output timing of torque based on the delay.

In some example embodiments, the gait motion of the user includes a left hip joint angle and a right hip joint angle of the user.

In some example embodiments, the method further includes filtering the gait motion of the user.

In some example embodiments, the generating the torque profile determines an output timing of torque based on the delay and a time delay associated with the filtering.

Some example embodiments relate to a walking assistance apparatus.

In some example embodiments, the walking assistance apparatus includes a controller configured to, define a state variable based on a result obtained by measuring a gait motion of a user, and generate a torque profile based on the state variable, a gain and a delay such that the torque profile assists the gait motion or resists to the gait motion based on the gain.

Some example embodiments relate to a walking assistance apparatus.

In some example embodiments, the walking assistance apparatus includes a sensor configured to measure a gait motion of a user; and a controller configured to, define a state variable based on the gait motion, generate a torque profile based on the state variable, a gain and a delay that is associated with the state variable, and control a driver based on the torque profile such that the driver outputs torque to resist the gait motion based on the torque profile generated by the controller.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 8A is a diagram illustrating an example of a stability analysis map associated with the result of FIGS. 7A and 7B;

DETAILED DESCRIPTION

Figure 1:
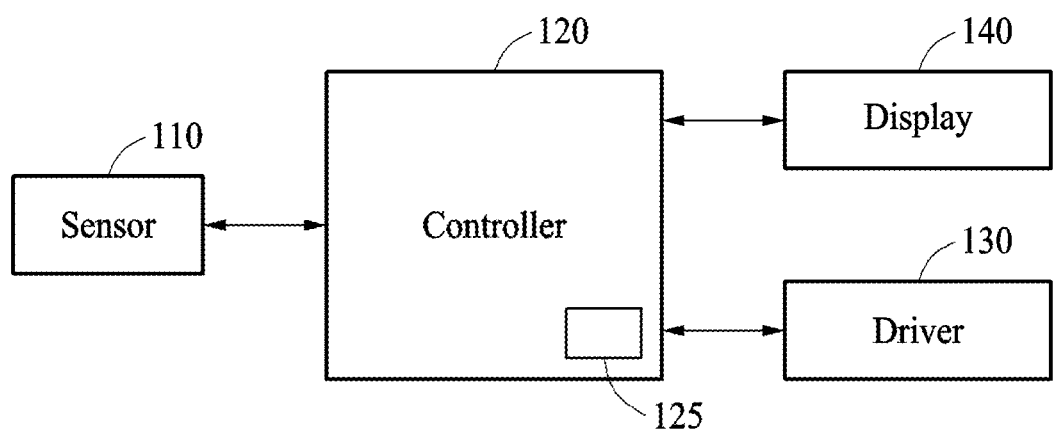
FIG. 1 is a block diagram illustrating a walking assistance apparatus according to at least one example embodiment.

The following structural or functional descriptions of some example embodiments disclosed in the present disclosure are merely intended for the purpose of describing the example embodiments and the example embodiments may be implemented in various forms. The example embodiments are not meant to be limited, but it is intended that various modifications are also covered within the scope of the claims.

Various modifications may be made to the example embodiments. However, it should be understood that these embodiments are not construed as limited to the illustrated forms and include all changes, equivalents or alternatives within the idea and the technical scope of this disclosure.

Although terms of "first," "second," etc. are used to explain various components, the components are not limited to such terms. These terms are used only to distinguish one component from another component. For example, a first component may be referred to as a second component, or similarly, the second component may be referred to as the first component within the scope of the right according to the example embodiments of the inventive concepts of the present disclosure.

It should be noted that if it is described in the specification that one component is "connected" or "coupled" to another component, a third component may be "connected" or "coupled" between the first and second components, although the first component may be directly connected or coupled to the second component. In addition, it should be noted that if it is described in the specification that one component is "directly connected" or "directly coupled" to another component, a third component may not be present therebetween. Likewise, expressions, for example, "between" and "immediately between" and "adjacent to" and "immediately adjacent to" may also be construed as described in the foregoing The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which these example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

A user of the walking assistance apparatus may be a patient who has a difficulty in walking normally, that is, who walks abnormally, for example, a patient who suffers from a stroke, a Charcot-Marie-Tooth (CMT) disease or a Parkinson's disease. A pathological gait or abnormal gait may refer to a gait to preserve an abnormal or pathological gait pattern through an adaptation of a human body system by sacrificing a normal gait pattern because the normal gait pattern collapses as a result of a functional disorder due to, for example, a partial injury, a weakness, a loss of flexibility, a pain, a bad habit, and a neural or muscular injury. The abnormal gait may indicate, for example, a pathological gait including at least one of abnormal gait types that will be described below.

The abnormal gait types may include, for example, at least one of a crouch gait (or a genu recurvatum gait), a steppage gait (or a footdrop gait), an antalgic gait, an ataxic gait, a festinating gait, a vaulting gait, a lurching gait, an equinus gait, a short leg gait, a hemiplegic gait, a circumduction gait, a tabetic gait, a neurogenic gait, a scissoring gait, or a parkinsonian gait.

The crouch gait may refer to walking with a posture in which all hip joints, knee joints and ankle joints are bent to overcome a gait instability. The steppage gait may refer to walking with a posture in which toes point downward on the ground and a top of a foot is dropped to the ground. The antalgic gait may refer to waling to lessen a pain on a painful portion. The ataxic gait may refer to walking with an uneven stride, a wide space between feet, a shaken body, and an unstable step appearing intoxicated. The festinating gait may refer to walking with a posture in which a trunk leans forward with a small stride without moving arms and an increase in a gait velocity as if it is impossible to stop walking. The vaulting gait may refer to walking using a leg of a non-affected side, for example, a non-paralyzed side, instead of a leg of an affected side, for example, a paralyzed side, when a knee joint is not extendable.

The lurching gait may refer to all staggering gaits, and may include, for example, a waddling gait, a gluteus maximus gait, or a Trendelenburg gait. The waddling gait may refer to swaying from side to side while walking. The gluteus maximus gait may refer to walking with a posture in which a chest is bent backward to maintain a hip extension and a whole trunk is suddenly moved from time to time. The Trendelenburg gait may refer to walking with a posture in which a chest tilts toward an injured leg to maintain a center of gravity and to prevent a pelvis of an injured side from drooping when standing on the ground with an injured lower limb.

The equines gait may refer to walking using tiptoes while heels are not in contact with the ground. The hemiplegic gait may refer to walking with a posture in which, due to a stiffness, an entire body is slightly tilted to an affected side, a swing of an upper arm in the affected side is lost and a lower limb appears in a primitively curved form in a state in which a shoulder of the affected side descends. The circumduction gait may refer to walking with a posture in which an entire leg swings due to a difficulty in bending a knee. The scissoring gait may refer to crossing or grazing legs or knees against to one another with a squatting posture in a state in which the legs are slightly bent inward. The Parkinsonian gait may refer to walking as if shuffling a sole on the ground with an anterior flexion posture.

Figure 2:
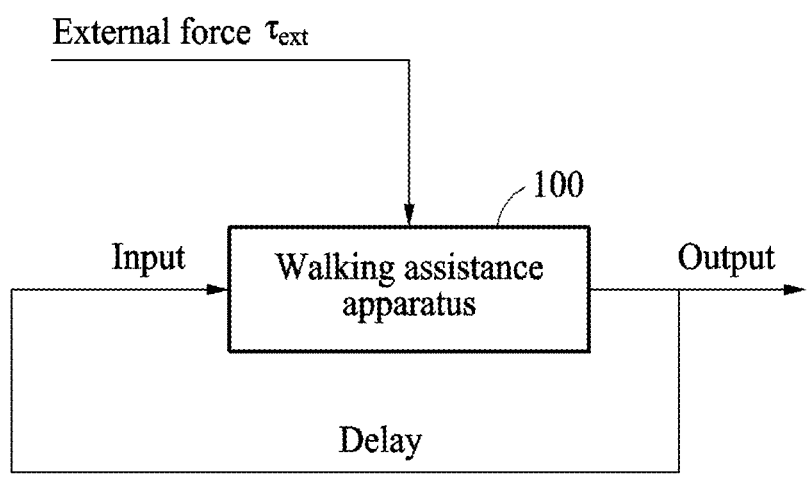
FIG. 2 is a diagram illustrating an operation of the walking assistance apparatus of FIG. 1.
Figure 3:
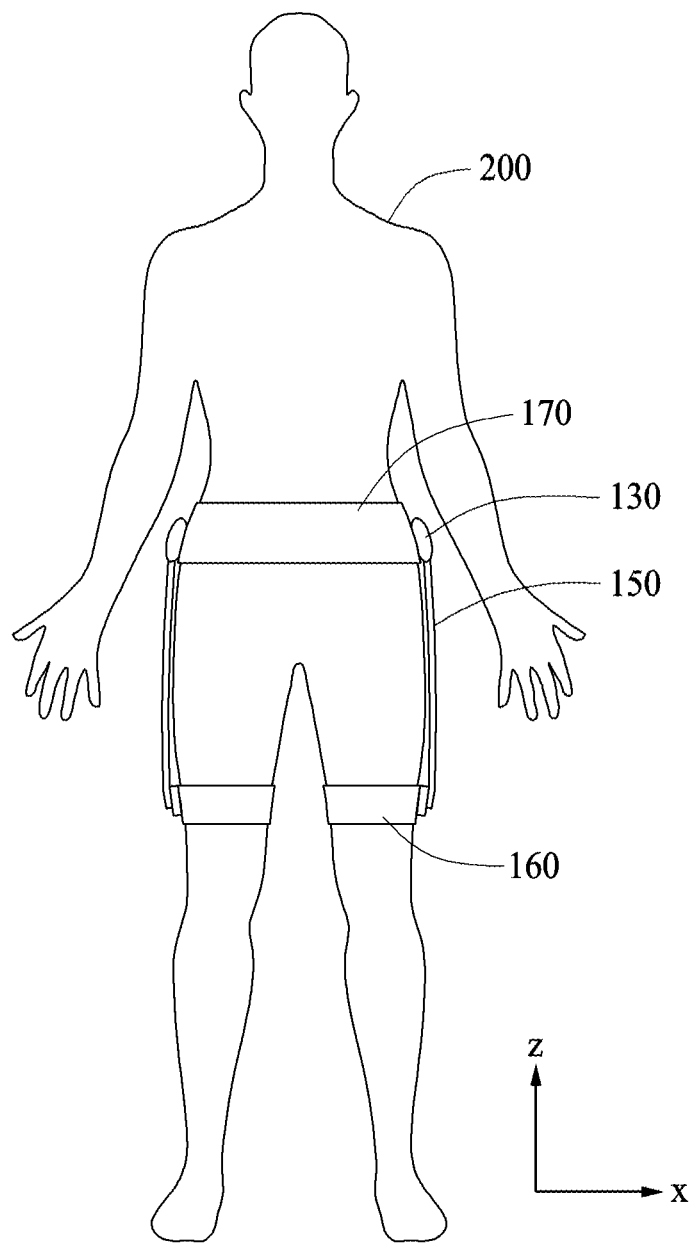
FIG. 3 is a front view illustrating the walking assistance apparatus of FIG. 1 worn on an object.

FIG. 1 illustrates a walking assistance apparatus 100 according to at least one example embodiment, and FIG. 2 illustrates an operation of the walking assistance apparatus 100. FIG. 3 is a front view illustrating the walking assistance apparatus 100 worn on an object, and FIG. 4 is a side view illustrating the walking assistance apparatus 100 worn on the object.

Referring to FIGS. 1 through 4, the walking assistance apparatus may include a sensor 110, a controller 120, a driver 130 and a display 140. Also, the walking assistance apparatus 100 may further include a filter (not shown), a force transmitting member 150, a supporting member 160, and a fixing member 170.

The walking assistance apparatus 100 may be worn on an object, for example, a user 200, to assist a gait and/or a motion of the user 200. The object may be, for example, a human, an animal or a robot, and there is no limitation thereto.

Figure 4:
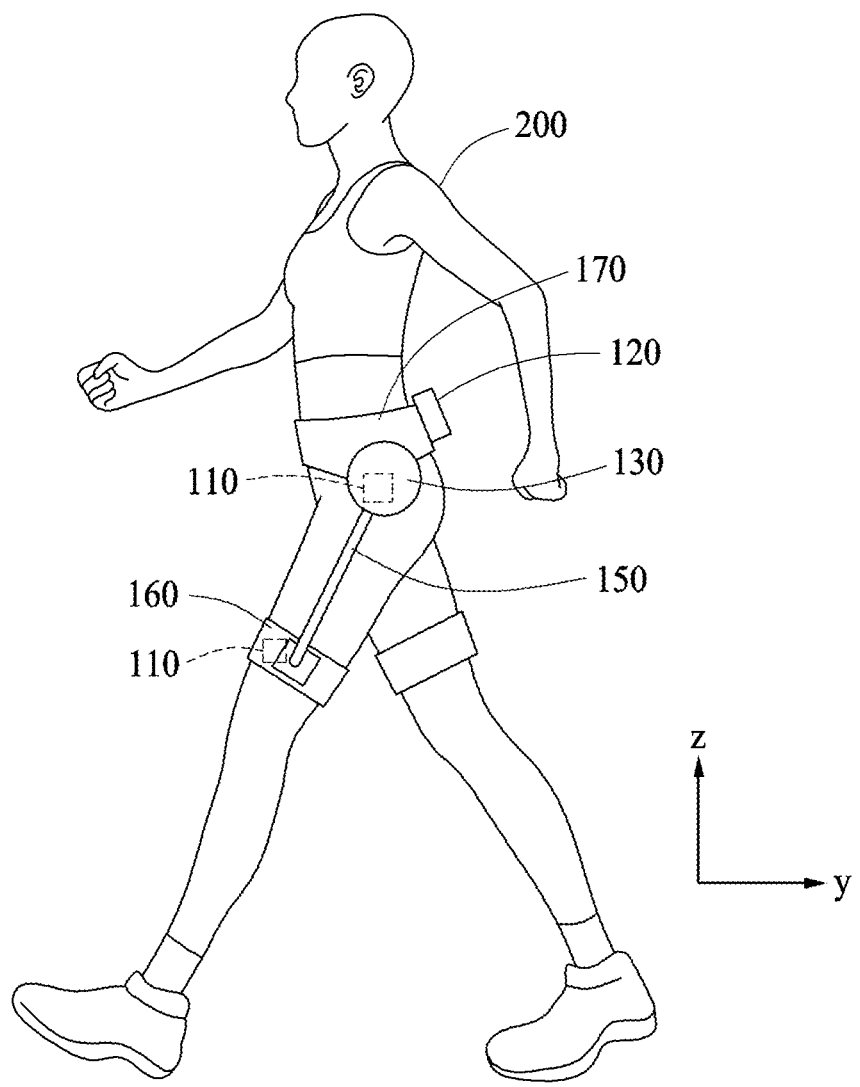
FIG. 4 is a side view illustrating the walking assistance apparatus of FIG. 1 worn on the object.

While FIGS. 3 and 4 illustrate a hip-type walking assistance apparatus, when the walking assistance apparatus 100 is worn on a thigh of the user 200, however, a type of the walking assistance apparatus 100 is not limited thereto. For example, the walking assistance apparatus 100 may be worn on at least one part of the upper body of the user 200, for example, a hand, an upper arm or a lower arm, or on at least one part of the lower body of the user 200, for example, a foot or a calf, and may assist a gait and/or motion of the user 200. The walking assistance apparatus 100 may be applicable to, for example, a walking assistance apparatus for supporting a portion of a pelvic limb, a walking assistance apparatus for supporting up to a knee, and a walking assistance apparatus for supporting up to an ankle, or a walking assistance apparatus for supporting a whole body.

The walking assistance apparatus 100 may assist a gait and/or a motion of another part of an upper body of the user 200, for example, a hand, an upper arm or a lower arm, or may assist a gait and/or a motion of another part of a lower body of the user 200, for example, a foot, a calf or a thigh. Thus, the walking assistance apparatus 100 may assist a gait and/or a motion of a part of the user 200.

As discussed in more detail below, the walking assistance apparatus 100 may measure a current gait motion of the user 200. When the walking assistance apparatus 100 measures the current gait motion, an external force $\tau_{ext}$ due to an interaction between the walking assistance apparatus 100 and the user 200 may also be measured. The walking assistance apparatus 100 may define a state variable y based on the current gait motion. The walking assistance apparatus 100 may set a delay $\Delta t$ for the state variable y. The delay $\Delta t$ may be a feedback element. In some example embodiments, the delay $\Delta t$ may be a time value set in advance by a user, and, in other example embodiments, the walking assistance apparatus 100 may automatically determine the delay $\Delta t$. The walking assistance apparatus 100 may generate a torque profile based on the state variable y and the delay $\Delta t$. The walking assistance apparatus 100 may output an assistance torque based on the torque profile, to assist a gait and/or motion of the user 200.

The walking assistance apparatus 100 may continue to perform an assistance operation by measuring the current gait motion of the user 200 assisted by the walking assistance apparatus 100.

The sensor 110 may include a first sensor configured to measure hip joint angular information associated with a right hip joint, and a second sensor configured to measure hip joint angular information associated with a left hip joint angle. The hip joint angular information may include at least one of hip joint angles of the hip joints, a difference between the hip joint angles, directions of motions for the hip joints, or angular velocity information for the hip joints.

The sensor 110 may be implemented as, for example, a hall sensor. In other example embodiments, the sensor 110 may include a potentiometer that senses an R-axis joint angle and an L-axis joint angle, and an R-axis joint angular velocity and an L-axis joint angular velocity based on a walking motion of the user.

As shown in FIG. 4, the sensor 110 may be implemented in at least one of the driver 130, the force transmitting member 150 or the supporting member 160.

The sensor 110 may transmit the hip joint angular information to the controller 120 via a wire or wirelessly.

The filter (not shown) may perform filtering of the hip joint angular information representing the current gait motion. The filter may be implemented as, for example, a low-pass filter (LPF). The filter may perform low-pass filtering of the hip joint angular information to remove noise from the hip joint angular information. The noise present in the hip joint angular information may be, for example, user movement and/or ground contact external shock. For example, the filter (not shown) may perform low pass filtering on the measurement results of the user's left hip joint angle and the right hip joint angle. Through this low-pass filtering, waveform of assistance torque or waveform of resistance torque can be smoothed. As will be described later, the assistance torque indicates a torque for assisting the user's walking, and the resistance torque indicates a torque for giving resistance to the user's walking. In addition, time delay (e.g., 0.1 second~0.2 second) may occur due to the low-pass filtering. However, since the walking assist device 100 intentionally uses the delay $\Delta t$ to be described later to generate the torque profile, the time delay due to the low-pass filtering is not a problem for the walking assistance or the walking resistance.

The controller 120 may include processing circuitry (not shown) and the memory 125.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design or execution of computer readable instructions stored in the memory, as a special purpose computer to perform the operations illustrated in FIG. 13 and the sub-operations thereof, discussed below.

The controller 120 may control an overall operation of the walking assistance apparatus 100. For example, the controller 120 may control the driver 130 to output a force to assist a gait of the user 200. The force may refer to a force used to extend or flex legs of the user 200. Also, the force may be, for example, an assistance torque.

The controller 120 may define a state variable based on the current gait motion received from the sensor 110. For example, the controller 120 may receive the current gait motion as feedback from the sensor 110, and may define the state variable. Also, the controller 120 may generate a torque profile based on the state variable.

The controller 120 may control the driver 130 to start to assist a gait of the user 200 based on the torque profile. The controller 120 may initiate an output of the torque profile to assist the gait of the user 200. Also, the controller 120 may control the driver 130 to terminate assistance of the gait. The controller 120 may terminate the output of the torque profile.

The controller 120 may control an assistance torque output by the driver 130 to the user based on the torque profile. The controller 120 may control an assistance torque that is output immediately in response to a current motion of the user 200, to prevent a mismatch between the user 200 and the walking assistance apparatus 100 in advance by flexibly coping with a sudden change in a motion of the user 200. Thus, the controller 120 may output a high assistance torque to the user 200 to actively assist a gait of the user 200.

The controller 120 may set a gain associated with a torque strength and a delay associated with a torque output time, and may define a state variable. For example, the controller 120 may control a strength of an assistance torque applied to the user 200 based on the gain, and may control a time at which the assistance torque is to be output based on the delay. In this example, the controller 120 may stably respond to a change in a surrounding environment or a sudden motion of the user 200 and stop of the motion, and may enhance a regularity and stability so that the user 200 may periodically walk.

The memory 125 be implemented as a volatile memory or a non-volatile memory. Examples of the volatile memory include, but are not limited to, RAM (random access memory), SRAM (static RAM), DRAM (dynamic RAM), SDRAM (synchronous DRAM), T-RAM (thyristor RAM), Z-RAM (zero capacitor RAM), or TTRAM (Twin Transistor RAM). Examples of the non-volatile memory include, but are not limited to, electrically erasable programmable read-only memory (EEPROM), flash memory, magnetic RAM (MRAM), spin-transfer torque MRAM, ferroelectric RAM (FeRAM), phase change RAM (PRAM), or RRAM (resistive RAM). Further, the nonvolatile memory may be implemented as a multimedia card (MMC), an embedded MMC (eMMC), a universal flash storage (UFS), a solid state drive (SSD), a USB flash drive, or a hard disk drive (HDD).

The memory 125 may store torque parameters corresponding to the torque profile output by the controller 120. The controller 120 may analyze a gait pattern of a user based on the torque parameters. Also, the controller 120 may output a periodic torque to assist a gait based on the torque parameters.

Although the memory 125 may be included in the controller 120 in FIG. 3, the memory 125 may be located outside the controller 120.

The driver 110 may include one or more motors that generate a rotational torque that is applied as a force to assist a gait of the user 200 based on a control of the controller 120, for example, based on the torque profile generated by the controller 120.

The driver 130 may drive both the hip joints of the user 200. The driver 130 may be located on, for example, a right hip portion and/or a left hip portion of the user 200.

The display 140 may be implemented as, for example, a touch screen, a liquid crystal display (LCD), a thin film transistor-liquid crystal display (TFT-LCD), a light emitting diode (LED) display, an organic LED (OLED) display, an active matrix OLED (AMOLED) display, or a flexible display.

The display 140 may display a user interface (UI) configured to control a gain and/or a delay to the user 200. For example, the user 200 may control, using the UI displayed on the display 140, a gain associated with a strength of an assistance torque and/or control a delay associated with a time at which the assistance torque is to be output.

The force transmitting member 150 may include, for example, a longitudinal member such as a frame, a wire, a cable, a string, a rubber band, a spring, a belt, or a chain.

The force transmitting member 150 may connect the driver 130 and the supporting member 160. The force transmitting member 150 may transmit the force from the driver 130 to the supporting member 160.

The supporting member 160 may support a target part, for example, a thigh of the user 200. The supporting member 160 may be disposed to cover at least a part of the user 200. The supporting member 160 may apply the force received from the force transmitting member 150 to a part of the user 200 to be supported.

The fixing member 170 may be attached to a part, for example, a waist of the user 200. The fixing member 170 may be in contact with at least a portion of an external surface of the user 200. The fixing member 170 may have a shape to cover the external surface of the user.

Figure 5A:
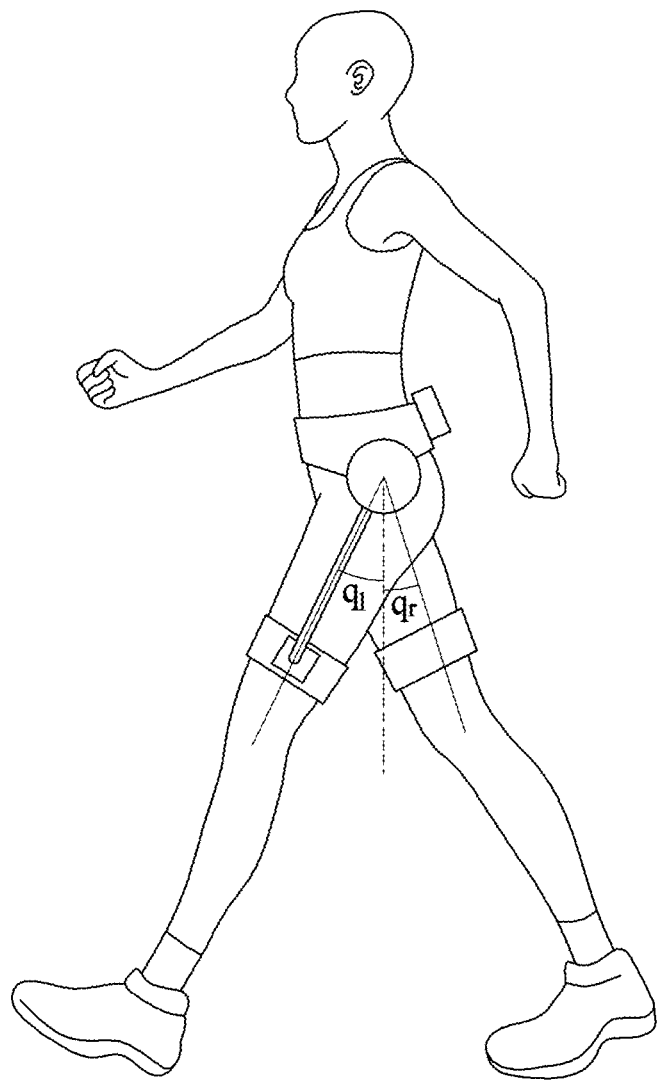
FIG. 5A is a diagram illustrating an example of an operation of a sensor and a controller of FIG. 1.
Figure 5B:
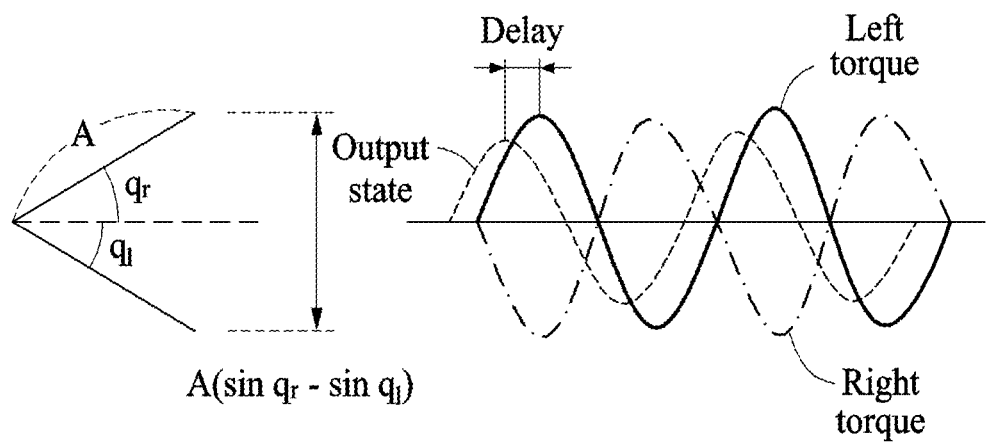
FIG. 5B is a diagram illustrating another example of an operation of the sensor and the controller of FIG. 1.

FIG. 5A illustrates an example of an operation of the sensor 110 and the controller 120 of FIG. 1, and FIG. 5B illustrates another example of an operation of the sensor 110 and the controller 120.

Referring to FIGS. 5A and 5B, the sensor 110 may measure the hip joint angular information as the current gait motion of the user 200. The current gait motion may include a left hip joint angle $q_l$ and a right hip joint angle $q_r$. The sensor 110 may measure the left hip joint angle $q_l$ and the right hip joint angle $q_r$, and may transmit the left hip joint angle $q_l$ and the right hip joint angle $q_r$ to the controller 120.

The controller 120 may define a state variable (y) based on the left hip joint angle $q_l$ and the right hip joint angle $q_r$.

In an example, the controller 120 may define the state variable (y) based on a difference "$q_r - q_l$" between the left hip joint angle $q_l$ and the right hip joint angle $q_r$. Because the left hip joint angle $q_l$ and the right hip joint angle $q_r$ vary over time, the controller 120 may define the state variable y using, for example, one of Equation 1 to Equation 3, discussed below.

For example, in some example embodiments, the controller 120 may define the state variable y using Equation 1:

$$y_1(t) = q_r(t) - q_l(t) \quad \text{[Equation 1]}$$

In Equation 1, $y_1(t)$ denotes the state variable, $q_r(t)$ denotes the right hip joint angle, and $q_l(t)$ denotes the left hip joint angle.

In other example embodiments, the controller 120 may define a state variable in a form of a trigonometric function. The controller 120 may express the left hip joint angle $q_l$ by a first trigonometric function and may express the right hip joint angle $q_r$ by a second trigonometric function. The controller 120 may define the state variable y based on a difference between the first trigonometric function and the second trigonometric function.

The trigonometric function may be a sine function or a cosine function. For example, the controller 120 may define a difference "$\sin(q_r) - \sin(q_l)$" between the first trigonometric function and the second trigonometric function as the state variable y. Also, the controller 120 may limit a value of the state variable to a range of values equal to or less than "1."

For example, the controller 120 may define a state variable using a trigonometric function based on Equation 2 shown below.

$$y_2(t) = \sin q_r(t) - \sin q_l(t) \quad \text{[Equation 2]}$$

In Equation 2, $y_2(t)$ denotes the state variable, $q_r(t)$ denotes the right hip joint angle, and $q_l(t)$ denotes the left hip joint angle.

In still other example embodiments, the controller 120 may define the state variable y to include a gain A associated with a torque strength and a delay $\Delta t$ associated with a torque output time. For example, the controller 120 may define the state variable y using Equation 3 shown below.

$$y_3(t) = A(\sin q_r(t - \Delta t) - \sin q_l(t - \Delta t)) \quad \text{[Equation 3]}$$

In Equation 3, $y_3(t)$ denotes the state variable, $q_r(t)$ denotes the right hip joint angle, $q_l(t)$ denotes the left hip joint angle, A denotes the gain, and $\Delta t$ denotes the delay.

In some example embodiments, the delay may be a value set in advance by the user 200. For example, the user 200 may set a delay in a unit of time, for example, seconds (s) or milliseconds (ms), in advance. Thus, the user 200 may hardly feel an assistance delay and may feel a natural assistance torque matching a motion. The walking assistance apparatus 100 may set an assistance torque timing $(t-\Delta t)$ based on the delay $\Delta t$, and may enhance a stability by, for example, finely adjusting the maximum assistance torque generation timing to correspond to a maximum joint angle.

In other example embodiments, as discussed below, the controller 120 may automatically determine the delay $\Delta t$ based on, for example, a gait velocity and/or a gait acceleration of the user 200.

The controller 120 may generate a first torque profile based on the state variable. The controller 120 may control the driver 130 to output an assistance torque corresponding to the first torque profile to a left leg of the user 200.

Also, the controller 120 may generate a second torque profile by changing a sign of the first torque profile. The controller 120 may control the driver 130 to output an assistance torque corresponding to the second torque profile to a right leg of the user 200. The controller 120 may also output an assistance torque corresponding to a profile by exchanging the left leg and the right leg.

The controller 120 may differently set magnitudes of assistance torques that are to be output to the left leg and the right leg. For example, when the user 200 feels uncomfortable with the left leg and a greater assistance torque is required for the left leg, the controller 120 may set a great gain of the first torque profile corresponding to the left leg. In this example, the driver 130 may output a greater assistance torque to the left leg rather than the right leg.

Hereinafter, experimental results of a walking assistance method performed by the walking assistance apparatus 100 based on the delay Δt (or, alternatively, the delay Δt and gain a) according to example embodiments is described with reference to FIGS. 6A to 12.

Figure 6A:
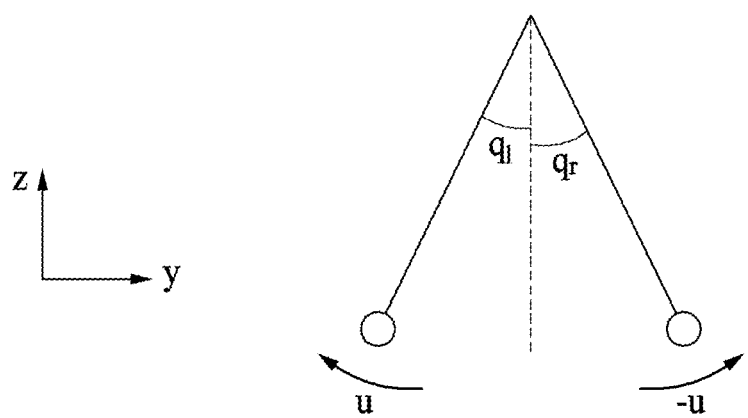
FIG. 6A is a diagram illustrating an example for evaluation of a performance of the walking assistance apparatus of FIG. 1.
Figure 6B:
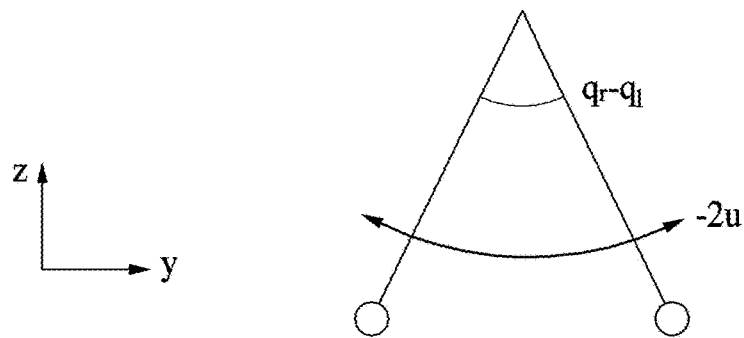
FIG. 6B is a diagram illustrating another example for evaluation of the performance of the walking assistance apparatus of FIG. 1.
Figure 7A:
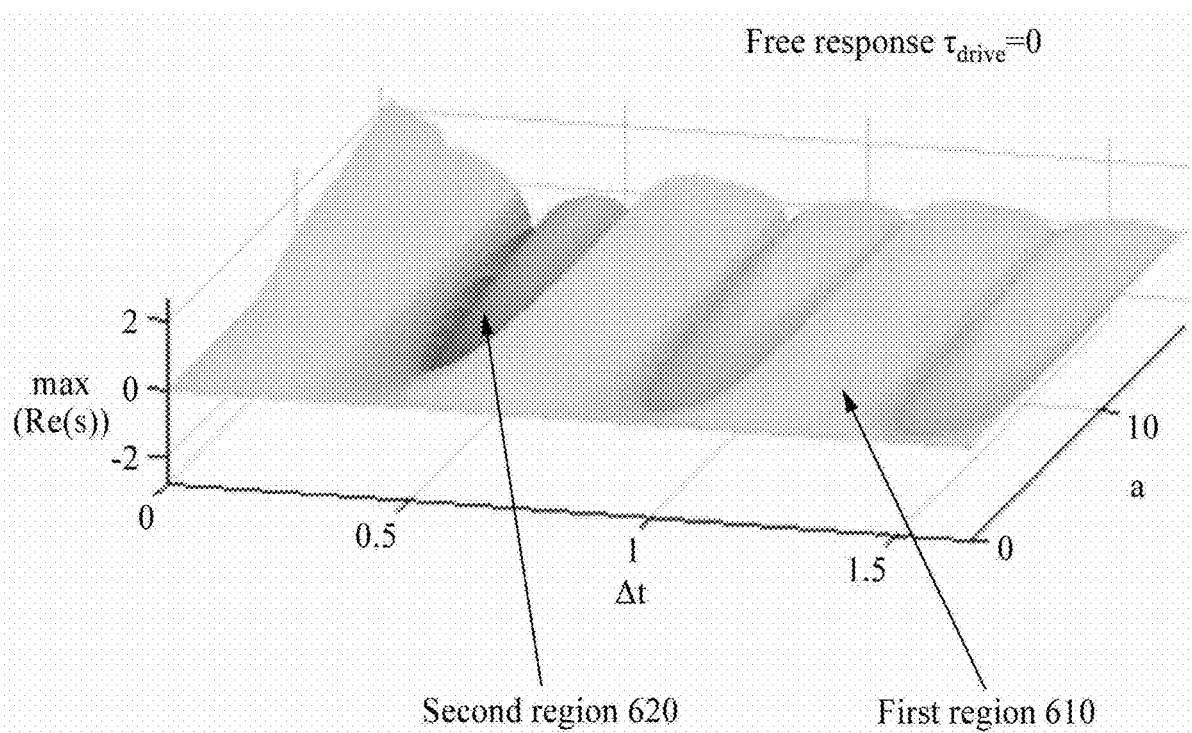
FIGS. 7A and 7B are a three-dimensional (3D) graph and a two-dimensional (2D) graph illustrating a result obtained by evaluating the performance of the walking assistance apparatus of FIG. 1, respectively.
Figure 7B:
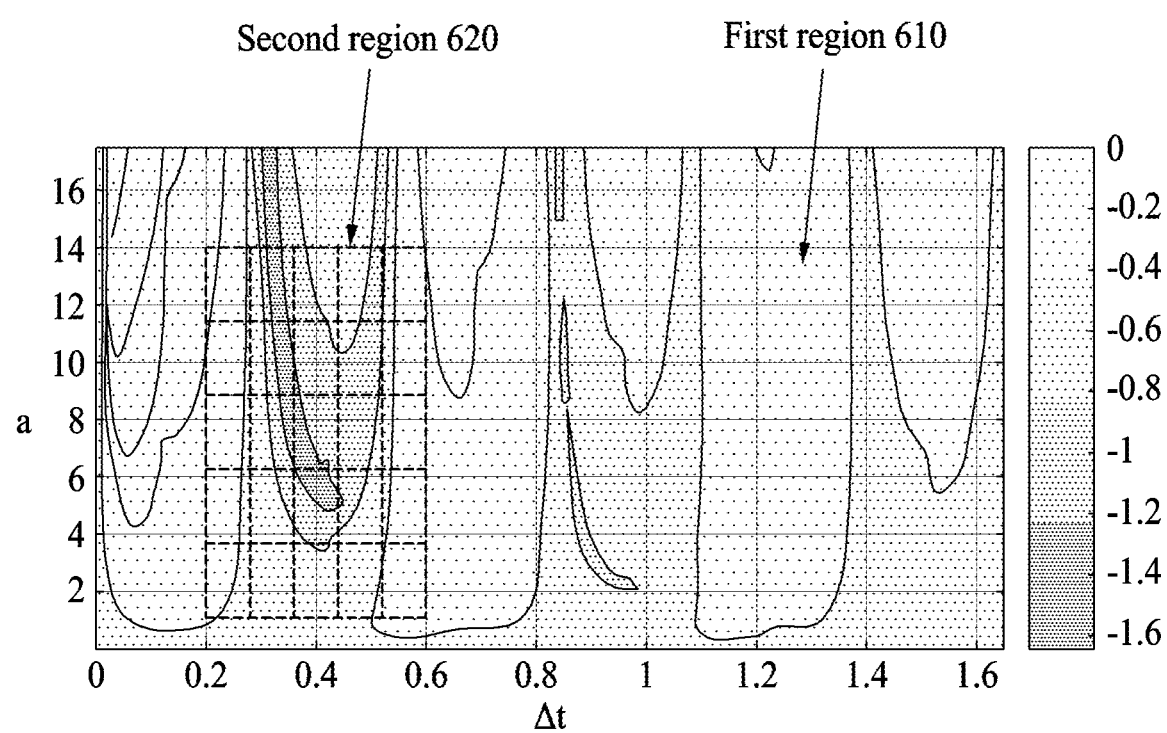
Figure 8B:
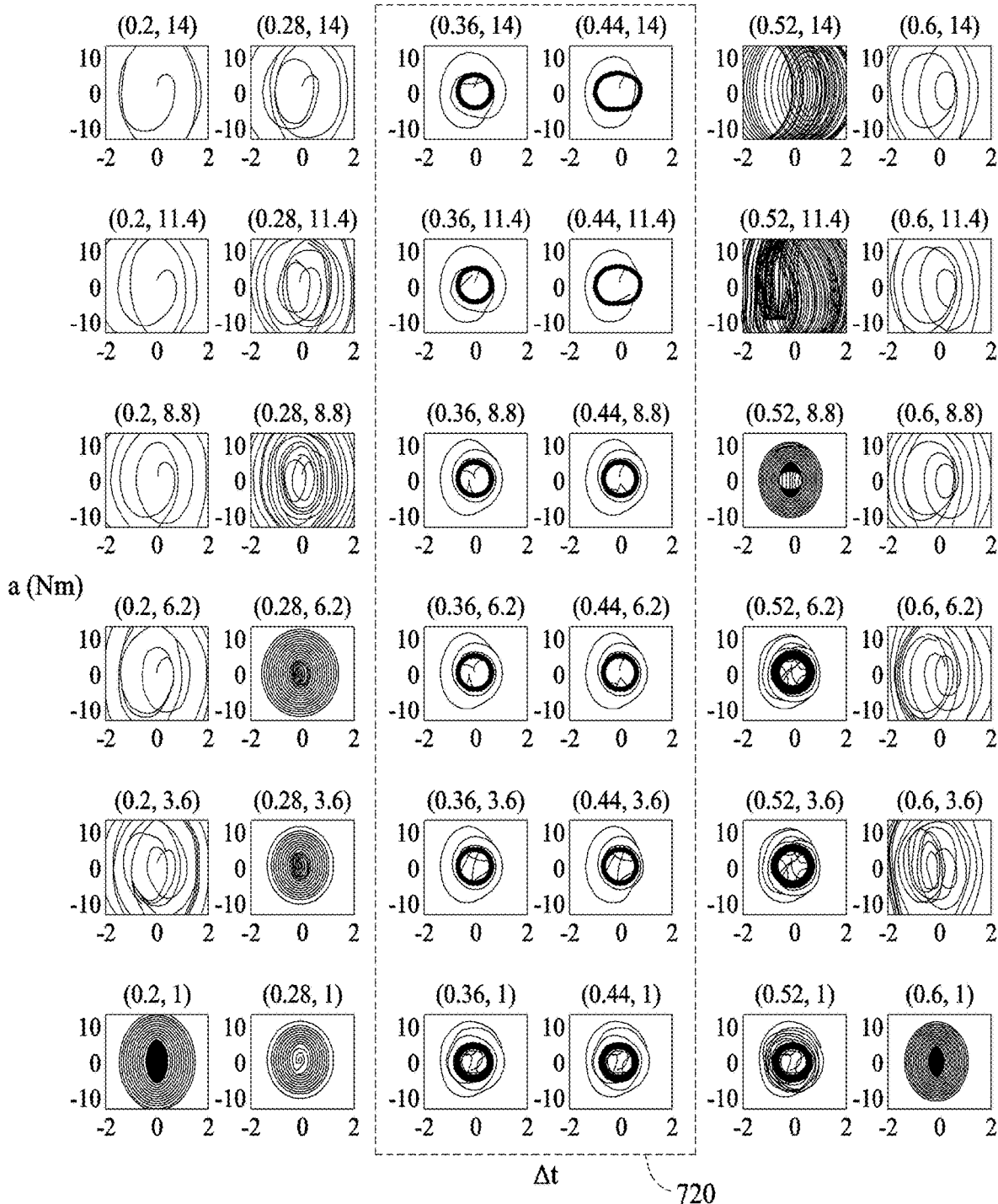
FIG. 8B is a diagram illustrating another example of a stability analysis map associated with the result of FIGS. 7A and 7B.

FIG. 6A illustrates an example for evaluation of the performance of the walking assistance apparatus 100 of FIG. 1 and FIG. 6B illustrates another example for evaluation of the performance of the walking assistance apparatus 100. FIGS. 7A and 7B are a three-dimensional (3D) graph and a two-dimensional (2D) graph illustrating a result obtained by evaluating the performance of the walking assistance apparatus 100, respectively. FIG. 8A illustrates an example of a stability analysis map associated with the result of FIGS. 7A and 7B, and FIG. 8B illustrates another example of a stability analysis map associated with the result of FIGS. 7A and 7B.

Referring to FIGS. 6A through 8B, the performance of the walking assistance apparatus 100 may be evaluated using simplified swing leg dynamic models. When an equivalent transformation is performed in the example of FIG. 6A, a result may be obtained as shown in FIG. 6B. In FIGS. 6A and 6B, $q_r$ denotes the right hip joint angle, $q_l$ denotes the left hip joint angle, and u denotes an exoskeleton driven torque.

To evaluate the stability of the walking assistance apparatus 100, modeling of a differential equation may be performed with respect to swinging of the left leg and right leg based on the torsion constant K, the moment of inertia I, the mass M, the period T, and the gait angular frequency w as shown in Equation 4 below.

For example, based on a user who is 165 centimeters tall and weighs 55 kilograms, constants used in dynamic modeling may be $I=I_{leg}\approx1$ kgm² K=MgL$_c$=30 kgm², L$_c$=0.3483 m², M=8.8550 kg $$T_0 = \frac{2\pi}{\sqrt{K/I}} = 1.15 \text{ s, and } w_0 = \sqrt{K/I} = 5.5 \text{ s}^{-1}.$$

$$I\ddot{q}_r(t)+B\dot{q}_r(t)+K\sin q_r(t)=-u(t)$$

$$I\ddot{q}_l(t)+B\dot{q}_l(t)+K\sin q_l(t)=u(t)$$

$$u(t)=Ay(t-\Delta t)$$

$$y(t)=\sin q_r(t)-\sin q_l(t) \quad \text{[Equation 4]}$$

An approximation may be performed and expressed by sin q≈q. When u(t) is subtracted from −u(t) in Equation 4, Equation 5 may be obtained.

$$\ddot{y}(t)+b\dot{y}(t)+ky(t)=-2ay(t-\Delta t)+\tau_{ext}$$

$$y(t)=q_r(t)-q_l(t) \quad \text{[Equation 5]}$$

In Equation 5, $\tau_{ext}$ denotes an external force exerted by an interaction between the walking assistance apparatus 100 and a user, and may be expressed by Equation 6 below.

$$\tau_{ext} = \tau_{regist} + \tau_{drive} \quad \text{[Equation 6]}$$
$$= (-k_{ext}y(t) - b_{ext}\dot{y}(t)) + a_{ext}\cos(wt)$$

In Equation 6, $\tau_{regist}$ denotes an external force due to resistance, $\tau_{drive}$ denotes an external force during walking, w denotes an gait angular frequency of a user expressed by $$\frac{2\pi}{T_{ext}},$$

a denotes an input torque expressed by A/I, k denotes a stiffness coefficient of "30" expressed by K/I, and b denotes a damping coefficient of "0.01" expressed by B/I.

An approximated characteristic equation may be expressed using a Lambert function as shown in Equation 7 below.

$$\dot{y}(t) = A_0 y(t) + A_1 y(t-\Delta t) \quad \text{[Equation 7]}$$

$$A_0 = \begin{bmatrix} -b-b_{ext} & -k-k_{ext} \\ 1 & 0 \end{bmatrix}$$

$$A_1 = \begin{bmatrix} 0 & -2a \\ 0 & 0 \end{bmatrix}$$

$$sI = \frac{1}{\Delta t}W(A_1\Delta t e^{-A_0\Delta t}) + A_0$$

$$eig\left\{\frac{1}{\Delta t}W(A_1\Delta t e^{-A_0\Delta t}) + A_0\right\}$$

Lambert function $W, z = W(ze^z)$

In Equation 7, the stability of the walking assistance apparatus 100 may be determined based on whether a maximum value of a real part of a solution of the characteristic equation is a negative number. Maximum real values of complex eigenvalues corresponding to the solution of the characteristic equation may be expressed by the 3D graph of FIG. 7A and the 2D graph of FIG. 7B.

Referring to FIGS. 7A and 7B, a first region 610 may indicate an unstable region. The first region 610 may be a non-negative region. For example, a plurality of first regions 610 may be present.

When the controller 120 sets the gain a and the delay Δt corresponding to the first region 610, the walking assistance apparatus 100 may be determined to be unstable due to a divergence or fluctuation in a stability analysis map because a stable focus or a stable limit cycle is not shown. The stable limit cycle may refer to a regular and repetitive pattern that converges to a periodic motion in association with a gait control.

In FIGS. 7A and 7B, a second region 620 may include a stable region. When the controller 120 sets the gain a and the delay Δt corresponding to the second region 620, a stability analysis map in a free response experiment and a stability analysis map in a forced response experiment of the walking assistance apparatus 100 may be shown in FIGS. 8A and 8B, respectively.

For example, the free response experiment may be a stability experiment conducted when a user stops walking. In the free response experiment, the external force $\tau_{drive}$ may be zero during walking.

The forced response experiment may be a stability experiment conducted during a continuous gait. For example, in the forced response experiment, the external force $\tau_{drive}$ may be $a_{ext}$ cos (wt).

For example, the second region 620 may include a third region 710, illustrated in FIG. 8A, or a fourth region 720, illustrated in FIG. 8B. When the controller 120 sets the gain a and the delay Δt corresponding to the third region 710 or the fourth region 720, a stable focus may be shown in the free response experiment and a stable limit cycle may be shown in the forced response experiment. In this example, the walking assistance apparatus 100 may allow a user to maintain regular walking.

Figure 9A:
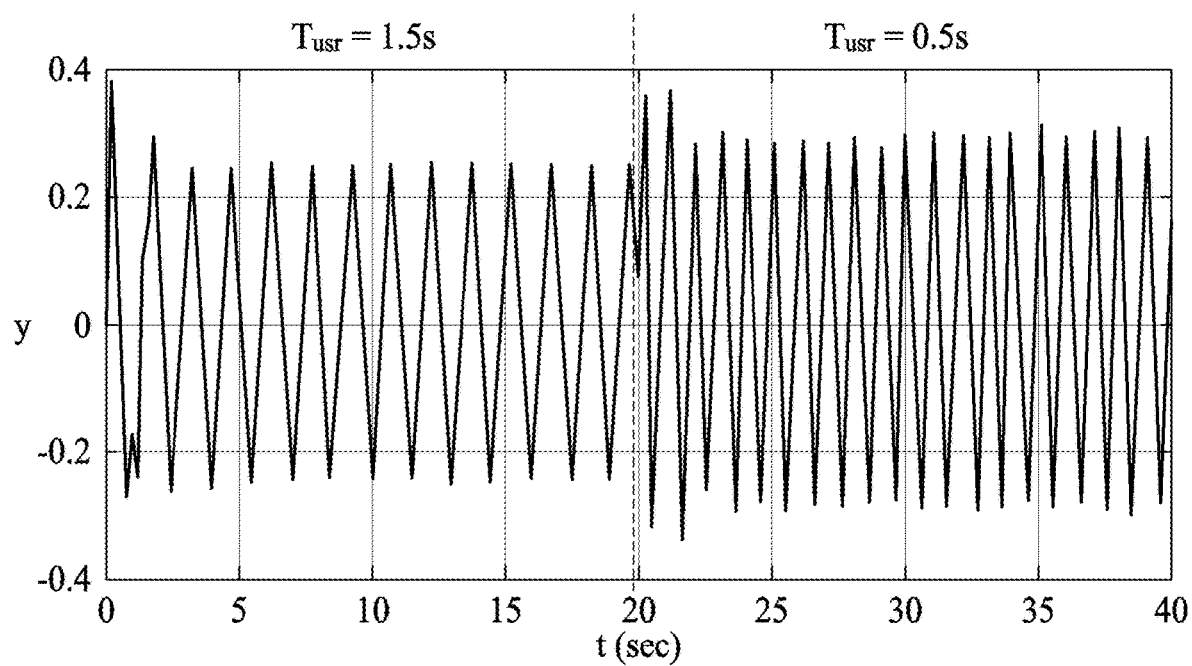
FIG. 9A is a graph illustrating a result of an experiment on a change in a gait velocity of a user according to at least one example embodiment.
Figure 9B:
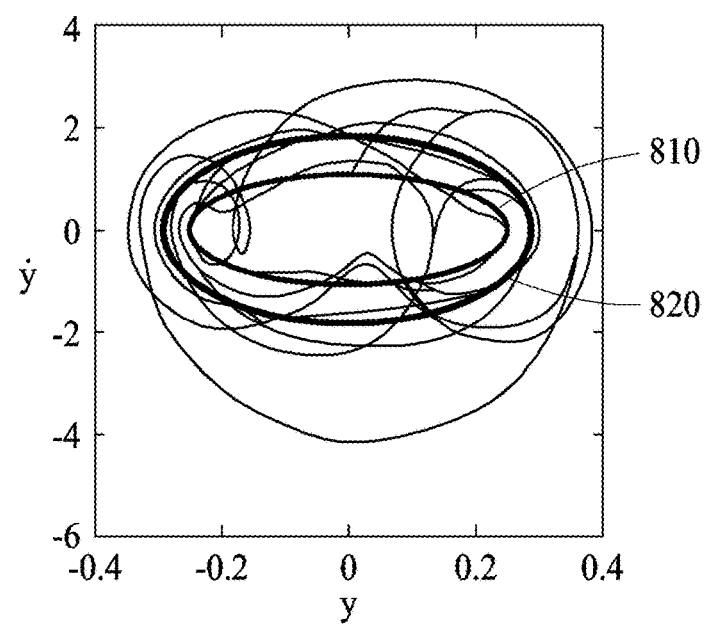
FIG. 9B is a diagram illustrating a stability analysis map associated with the result of FIG. 9A.

FIG. 9A is a graph illustrating a result of an experiment on a change in a gait velocity of a user according to at least one example embodiment, and FIG. 9B illustrates a stability analysis map associated with the result of FIG. 9A.

Referring to FIGS. 9A and 9B, FIGS. 9A and 9B illustrate a stability of the walking assistance apparatus 100 of FIG. 1 measured when the gait velocity of the user increases. For example, the user walks at an interval of 1.5 s and changes the gait velocity to quickly walk at an interval of 0.5 s after 20 s. In this example, the walking assistance apparatus 100 may show two stable limit cycles, that is, stable limit cycles 810 and 820 and may stably respond to a sudden change in a motion of the user. Thus, the walking assistance apparatus 100 may have a self-stabilizing characteristic.

Figure 10:
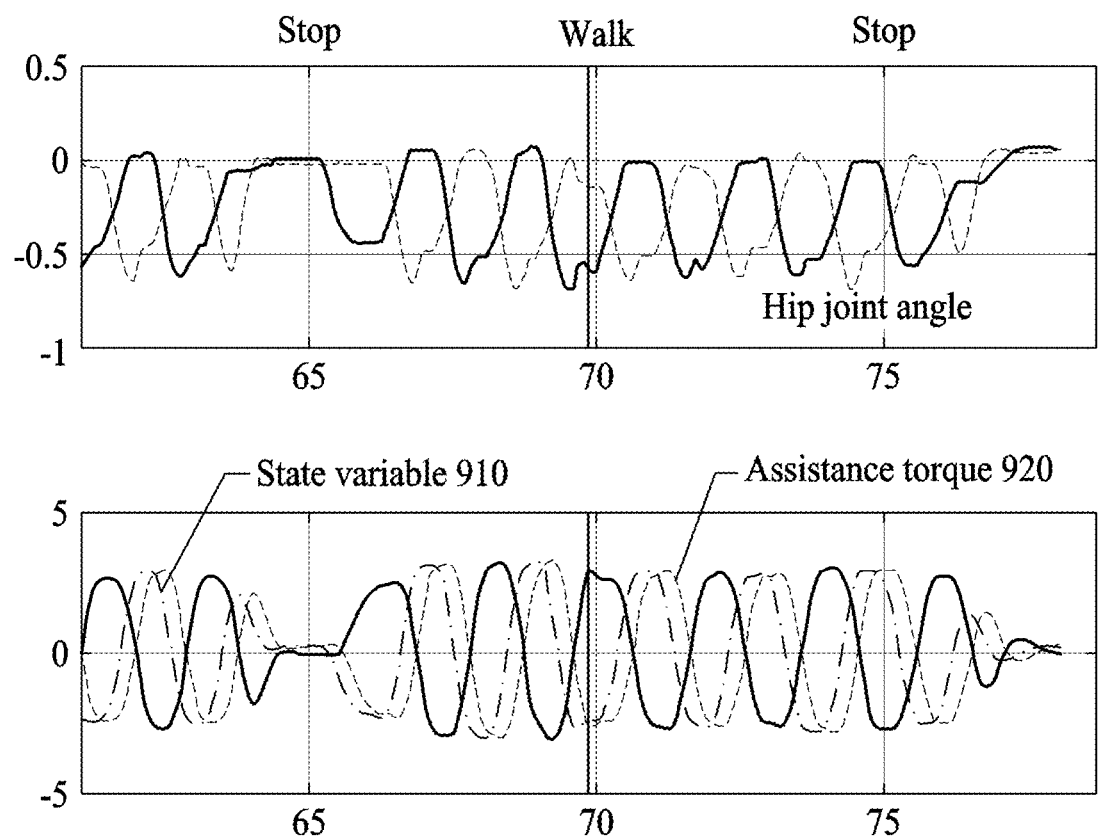
FIG. 10 illustrates experimental results when a user repeats walking and stopping according to at least one example embodiment.

FIG. 10 illustrates experimental results when a user repeats walking and stopping according to at least one example embodiment.

Referring to FIG. 10, when a user stops walking, a hip joint range of motion (ROM) decreases. For example, the user stops walking at 65 s and 75 s. In this example, it is found that the walking assistance apparatus 100 immediately responds to a stop of the user, by analyzing a state variable 910 and an assistance torque 920 of the walking assistance apparatus 100. Thus, the walking assistance apparatus 100 may exhibit a high stability by effectively responding to an intention of the user.

Also, it is found that when the user who is stationary wants to walk, the hip joint ROM increases. For example, the user starts walking at 66 s. In this example, it is found that the walking assistance apparatus 100 immediately responds to a gait change of the user, by analyzing the state variable 910 and the assistance torque 920.

Figure 11:
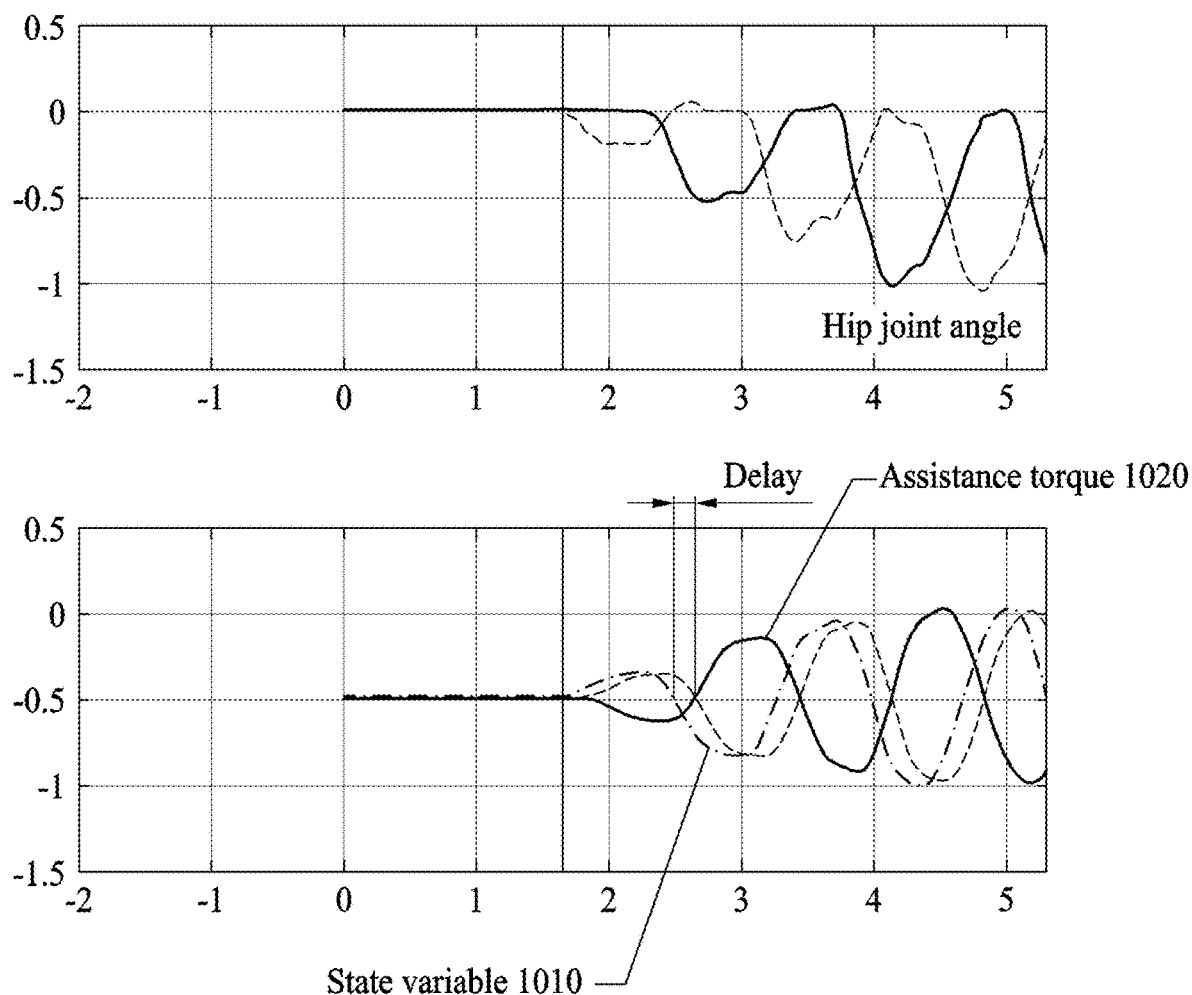
FIG. 11 illustrates experimental results when a user who is stationary wants to walk according to at least one example embodiment.

FIG. 11 illustrates experimental results when a user who is stationary wants to walk according to at least one example embodiment.

Referring to FIG. 11, when a user who is stationary wants to walk, a hip joint ROM increases. By analyzing a state variable 1010 and an assistance torque 1020 of the walking assistance apparatus 100, it is found that the walking assistance apparatus 100 immediately responds to a gait change of the user, as described above.

Figure 12:
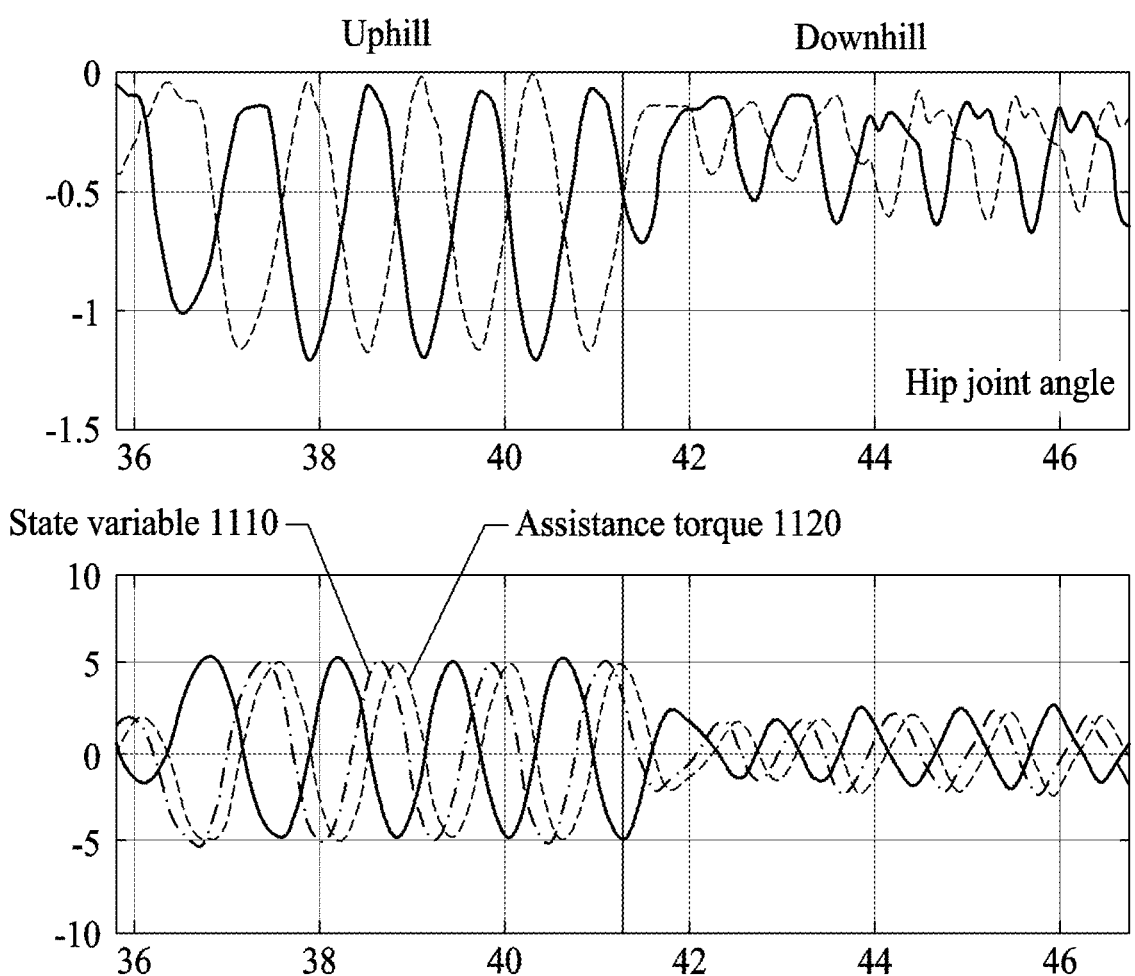
FIG. 12 illustrates experimental results when a user wants to walk uphill and then downhill according to at least one example embodiment.

FIG. 12 illustrates experimental results when a user wants to walk uphill and then downhill according to at least one example embodiment.

Referring to FIG. 12, when a user walks uphill and then downhill, a hip joint ROM rapidly changes. By analyzing a state variable 1110 and an assistance torque 1120 of the walking assistance apparatus 100, it is found that the walking assistance apparatus 100 immediately responds to a change in a walking environment of the user.

Figure 13:
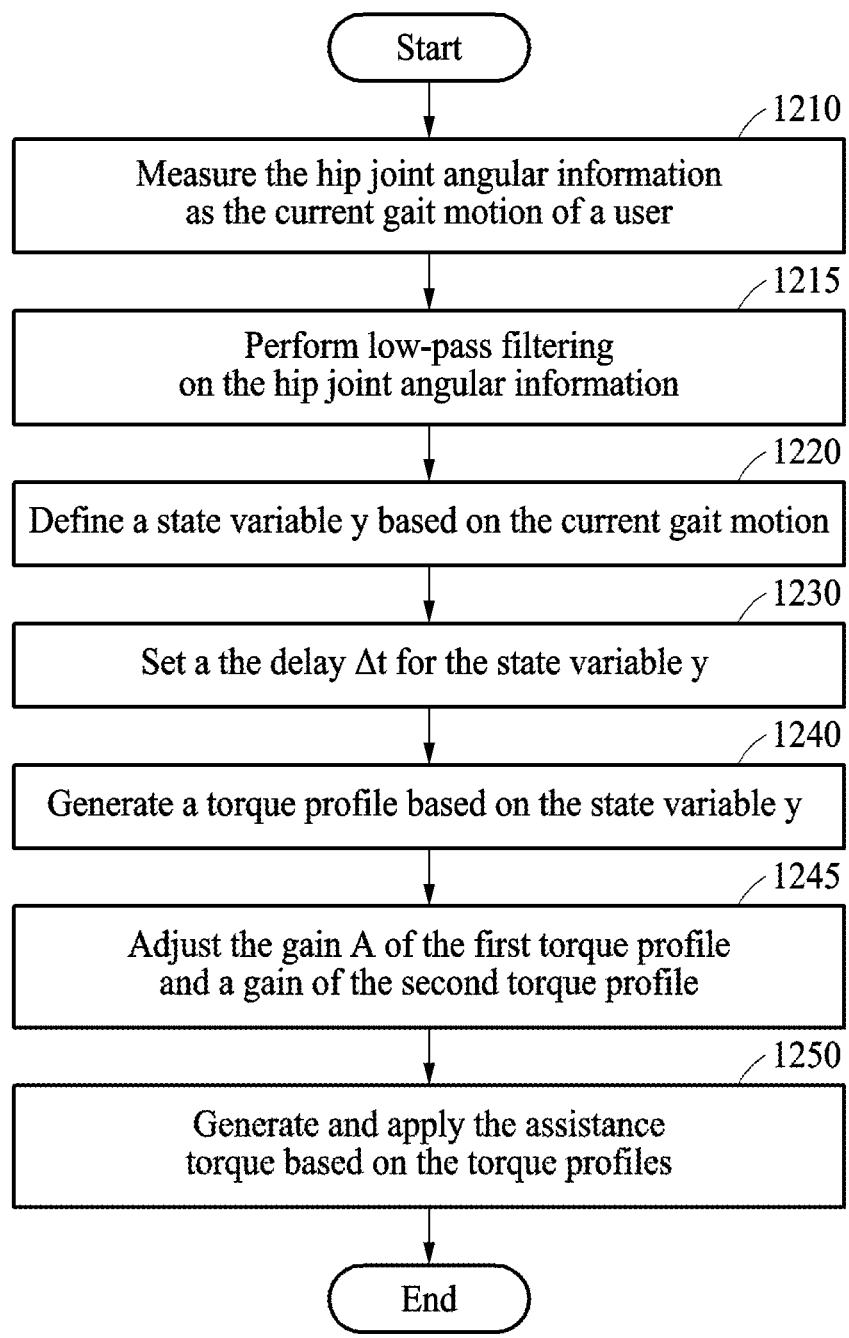
FIG. 13 is a flowchart illustrating a walking assistance method performed by the walking assistance apparatus of FIG. 1 according to at least one example embodiment.
Figure 14:
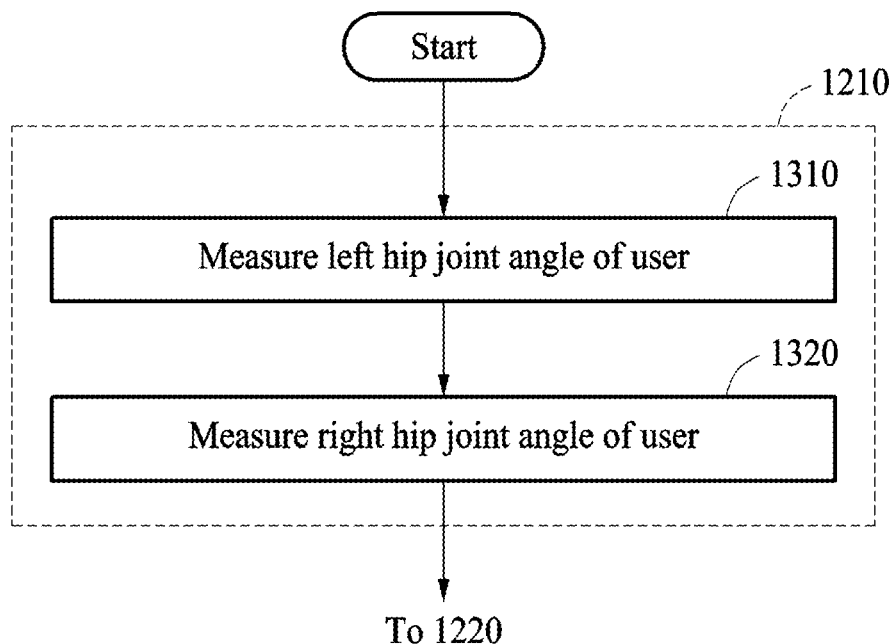
FIG. 14 is a flowchart illustrating an operation of measuring a current gait motion of a user in the walking assistance method of FIG. 13.
Figure 15:
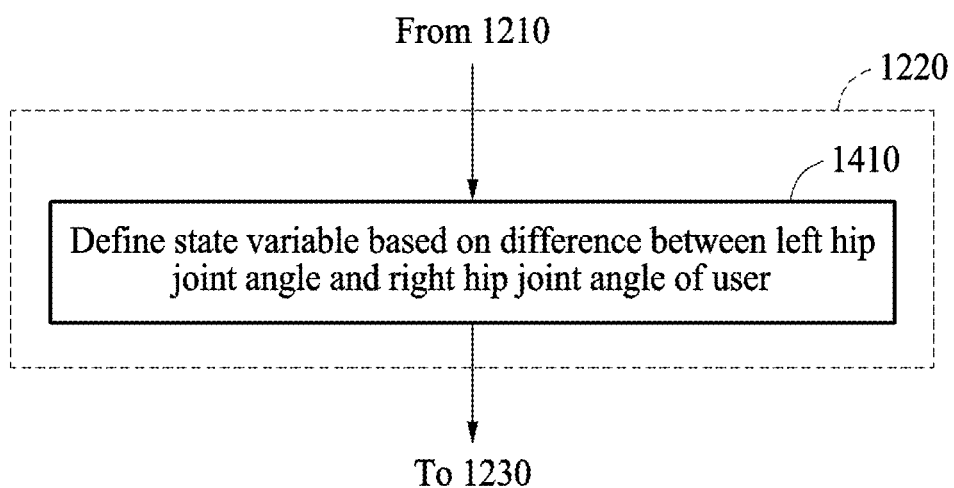
FIG. 15 is a flowchart illustrating an example of an operation of defining a state variable in the walking assistance method of FIG. 13.
Figure 16:
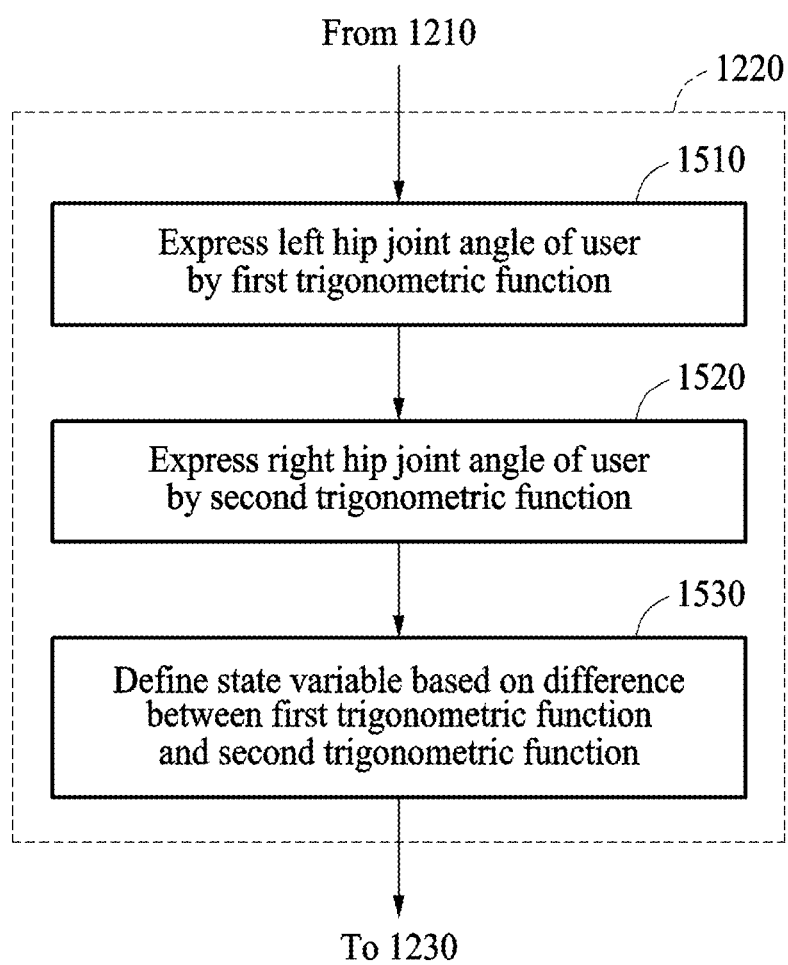
FIG. 16 is a flowchart illustrating another example of an operation of defining a state variable in the walking assistance method of FIG. 13.

FIG. 13 is a flowchart illustrating a walking assistance method performed by the walking assistance apparatus 100 of FIG. 1 according to at least one example embodiment. FIG. 14 is a flowchart illustrating an operation of measuring a current gait motion of a user in the walking assistance method of FIG. 13, FIG. 15 is a flowchart illustrating an example of an operation of defining a state variable in the walking assistance method of FIG. 13, and FIG. 16 is a flowchart illustrating another example of an operation of defining a state variable in the walking assistance method of FIG. 13.

Referring to FIGS. 13 through 16, in operation 1210, the walking assistance apparatus 100 may measure the hip joint angular information as the current gait motion of a user, while for example the user is ambulatory. The hip joint angular information may include hip joint angles.

For example, as illustrated in FIG. 14, in operation 1310, the sensor 110 measure the left hip joint angle $q_l$, and, in operation 1320, the sensor 110 may measure the right hip joint angle $q_r$. The sensor 110 may transmit the measured hip joint angles to the controller 120.

In some example embodiments, if the user has an abnormal gait type, the gait of the user may be defined by a user inclining their trunk and rotating their pelvis rather than their hip joint when walking. Therefore, in some example embodiments, the controller 120 may determine the hip joint angle by correcting the measured hip joint angles based on an inclination of a trunk of the user and a rotational angular velocity of a pelvis of the user.

Referring back to FIG. 13, in operation 1215, the walking assistance apparatus 100 may perform low-pass filtering on the hip joint angular information. For example, the controller 120 may apply the following equation to the left hip joint angle $q_l$ the right hip joint angle $q_r$.

$$q[i]=(1-\alpha)q[i-1]+\alpha q_{raw}[i], (0<\alpha<1)$$

Where $q_{raw}[i]$ is the hip joint angle measured by the sensor, α is a variable between zero and one, and q[i] is the low-pass filtered hip joint angular information.

In operation 1220, the walking assistance apparatus 100 may define a state variable y based on the current gait motion (e.g., $q_l$ and $q_r$). Such that the walking assistance apparatus 100 may utilize the current gait motion as feedback when defining the state variable.

For example, in some example embodiments, as illustrated in FIG. 15, in operation 1410, the controller 120 may receive the current gait motion (e.g., the hip joint angular information) as a feedback, define the state variable y based on a difference between the left hip joint angle and the right hip joint angle included in the hip joint angular information. For example, the controller 120 may utilize Equation 1, which represents the hip joint motion in joint space, to define the state variable y.

In other example embodiments, as illustrated in FIG. 16, the controller 120 may define the state variable y using a trigonometric function, such as Equation 2, which represents the hip joint motion in ground projected task space. In operation 1510, the controller 120 may express the left hip joint angle $q_l$ by a first trigonometric function. In operation 1520, the controller 120 may express the right hip joint angle $q_r$ by a second trigonometric function. In operation 1530, the controller 120 may define the state variable based on a difference between the first trigonometric function and the second trigonometric function.

Referring back to FIG. 13, in operation 1230, the walking assistance apparatus 100 may set the delay Δt for the state variable y. The delay Δt may be a feedback element.

For example, in some example embodiments, the controller 120 may receive the delay Δt, which is set in advance by a user. For example, the user may set a delay in a unit of time, for example, seconds (s) or milliseconds (ms), in advance.

In other example embodiments, the controller 120 may automatically determine the delay Δt adaptively.

For example, the controller 120 may determine the delay Δt based on a gait velocity of the user 200. The controller 120 may set a relatively short delay Δt in response to the gait velocity being greater than a first reference value, and may set a relative long delay Δt in response to the gait velocity being less than the first reference value. The controller 120 may measure the gait velocity based on the current gait motion received from the sensor 110.

In some other example embodiments, the controller 120 may determine the delay Δt based on the gait acceleration of the user 200. The controller 120 may set a relatively short delay Δt in response to the gait acceleration being greater than a second reference value, and may set a relatively long delay Δt in response to the gait acceleration being less than the second reference value.

In operation 1240, the walking assistance apparatus 100 may generate a torque profile based on the state variable y. For example, the walking assistance apparatus 100 may generate a first torque profile corresponding to a left leg. The walking assistance apparatus 100 may generate a second torque profile by changing a sign of the first torque profile. The walking assistance apparatus 100 may output an assistance torque to the left leg based on the first torque profile, and may output an assistance torque to a right leg based on the second torque profile.

In some example embodiments, the torque profile may include torque parameters Torque Start $1_{start}$, Torque Period $d_{ased}$, Torque Peak $1_{peak}$, Torque Quantity $\tau_{peak}$, Torque Peak Duration $d_{peak}$, and Torque Decrease Duration $d_{dsed}$.

In some example embodiments, the walking assistance apparatus 100 may adjust the torque profile/output torque based on the weight of the user. For example, the controller 120 may receive data from either a user input or from sensors indicating the weight of the users, and may increase or decrease the torque profile based on whether the weight of the user is above or below a threshold.

In operation 1245, the walking assistance apparatus 100 may adjust the gain A of the first (left) torque profile and a gain of the second (Right) torque profiles by adjusting the state variable.

For example, the controller 120 may utilize Equation 3 to determine the state variable y, and set the gain A applied to the state variable A based on, for example, user input.

For example, the controller 120 may display, via the display 140, a user interface (UI) configured to control the gain A. For example, the user 200 may control, using the UI displayed on the display 140, the gain A associated with a strength of an assistance torque. The controller 120 may utilize the gain A input by the user when calculating the state variable y.

Further still, in other example embodiments, during rehabilitation, a second user (e.g., a physical therapist), may set the gain A, for example, via a remote controller, as a negative value to gradually reduce the amount of assistance force provided over time.

In operation 1250, the walking assistance apparatus 100 may generate and apply the assistance torque based on the torque profile (or, alternatively the gain adjusted torque profile).

For example, the controller 120 may instruct the driver 130 to generate the assistance torque and apply the same to the body of the user to assist the user with walking.

Since the walking assistance apparatus 100 utilizes the delay Δt for feeding back the state variable y rather than a scheme of applying a predefined torque pattern based on a gait phase, the walking assistance apparatus 100 may match timing corresponding to swing at the maximum velocity (in the vicinity of a point in time at which left/right hip joints cross) with the timing of applying the maximum assistance torque. Further, due to the time delay Δt, the walking assistance apparatus 100 may quickly and reliably cope with sudden stopping or changes in a gait speeds or environmental changes (e.g., stairs and/or ramps), and abnormal gait patterns of a user (e.g., a gait pattern of user with a stroke, CMT or Parkinsons) without any additional sensors or computational processing. Thus, the user may hardly feel an assistance delay and may feel a natural assistance torque matching a motion.

In some example embodiments, prior to generating the assistance torque, the walking assistance apparatus 100 may select an abnormal gait type, and, in operation 1250, the controller may generate the assistance torque based on the torque profile and the selected abnormal gait type.

In some example embodiments, the abnormal gait type may be input by the user via, for example, a remote control.

In other example embodiments, rather than selecting an abnormal gait type. the walking assistance apparatus 100 may automatically estimate the abnormal gait type. For example, the controller 120 may utilize electromyogram (EMG) signals from muscles of the user and motion data from joints of the user to estimate the abnormal gait type.

Hereinafter, examples of systems implementing the walking assistance apparatus 100 will be described.

Figure 17:
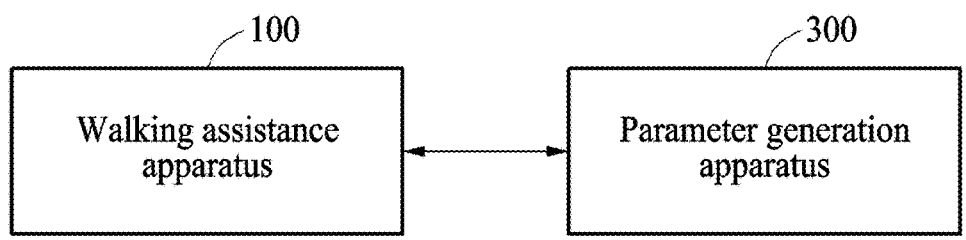
FIG. 17 is a block diagram illustrating an example of a walking assistance system according to at least one example embodiment.

FIG. 17 is a block diagram illustrating a walking assistance system 1600 according to at least one example embodiment.

Referring to FIG. 17, the walking assistance system 1600 may include the walking assistance apparatus 100 and a parameter generation apparatus 300.

The parameter generation apparatus 300 may analyze an existing gait pattern of a user, and may generate and store the torque parameters. The walking assistance apparatus 100 may receive the torque parameters from the parameter generation apparatus 300, and may generate the assistance torque based on the torque parameters.

The walking assistance apparatus 100 may receive the torque parameters using a feedforward scheme, and may receive a current gait motion using a feedback scheme. The walking assistance apparatus 100 may define the state variables based on the torque parameters and the current gait motion, may generate the torque profile based on the state variables, and may output the assistance torque based on the torque profile.

For example, a user may select a gait type of the user from a plurality of abnormal gait types using the display 140. The controller 120 may receive, in advance, the abnormal gait type of the user, and may output the assistance torque corresponding to the abnormal gait type.

Figure 18:
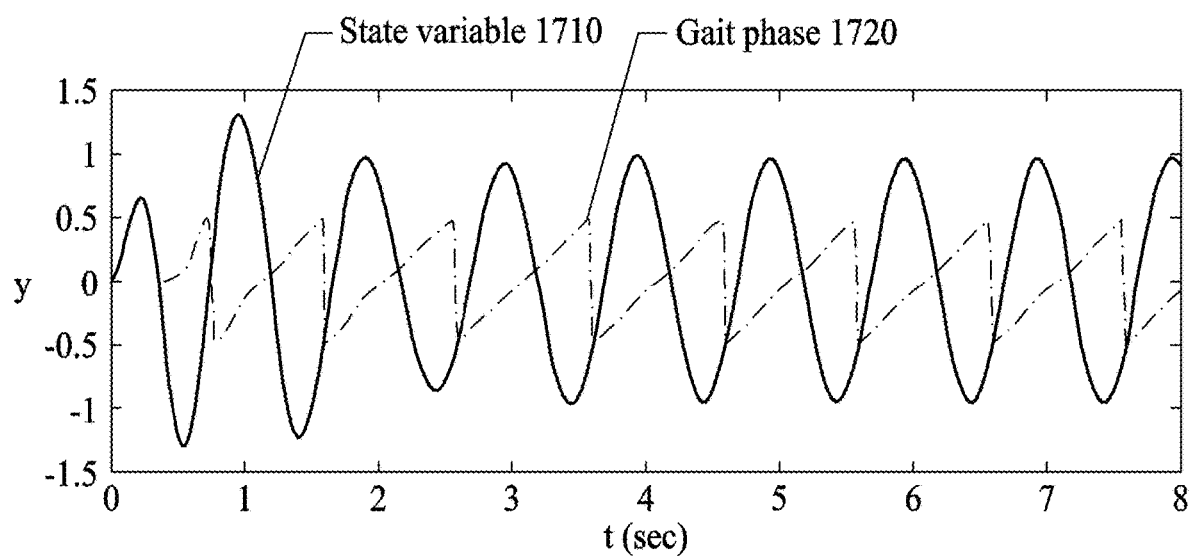
FIG. 18 is a graph illustrating an example of using the walking assistance apparatus 100 as a phase estimator according to at least one example embodiment.

FIG. 18 is a graph illustrating an example of using the walking assistance apparatus 100 as a phase estimator according to at least one example embodiment.

In FIG. 18, the walking assistance apparatus 100 may be used as a phase estimator. FIG. 18 illustrates a result obtained by estimating a gait phase 1720 of a user based on a state variable 1710 defined by the walking assistance apparatus 100. For example, the walking assistance apparatus 100 may estimate the gait phase 1720 using Equation 8 shown below.

$$\text{phase} = \frac{1}{2\pi}\text{atan2}(cy(t-\Delta t), \dot{y}(t-\Delta t)) \quad [\text{Equation 8}]$$

$$y(t) = \sin q_r(t) - \sin q_l(t)$$

In Equation 8, $\Delta t$ denotes the delay, and c denotes a scaling factor used to perform scaling.

While Equation 8 is shown utilizing Equation 2 to define the state variable y, example embodiments are not limited thereto. For example, in other example embodiments, the phase estimator may utilize Equation 1 to define the state variable y when determining the phase.

Figure 19:
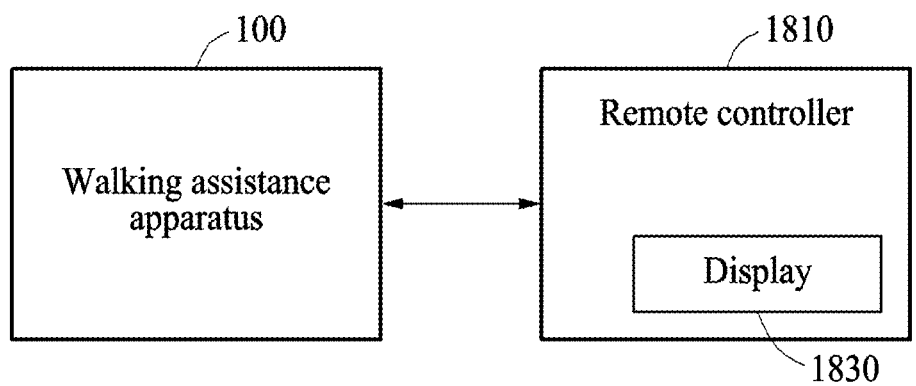
FIG. 19 is a block diagram illustrating another example of a walking assistance system according to at least one example embodiment.

Referring to FIG. 19, the walking assistance system 1800 may include the walking assistance apparatus 100 and a remote controller 1810.

The remote controller 1810 may control an overall operation of the walking assistance apparatus 100 in response to a user input. For example, the remote controller 1810 may initiate or stop an operation of the walking assistance apparatus 100. Also, the remote controller 1810 may control an output of a torque profile to control the walking assistance apparatus 100 to assist a gait of a user.

The remote controller 1810 may include a display 1830. The display 1830 may be implemented as, for example, a touch screen, an LCD, a TFT-LCD, an LED display, an OLED display, an AMOLED display or a flexible display.

The remote controller 1810 may provide a user with a UI and/or a menu corresponding to a function for operating the walking assistance apparatus 100, using the display 1830. For example, the remote controller 1810 may be a device for a manual operation of a user. For example, a user may select a start, stop or end of gait assistance. Also, the user may select an abnormal gait type and may receive a gait assistance based on the selection. The remote controller 1810 may receive an input from a user through the display 1830.

The display 1830 may include a touch screen that provides a UI or a menu. The display 1830 may display an operating state of the walking assistance apparatus 100 to the user under a control of the remote controller 1810. The operating state of the walking assistance apparatus 100 displayed by the display 1830 may include, for example, an output torque, a current gait motion of a user or an abnormal gait type selected by the user.

Figure 20:
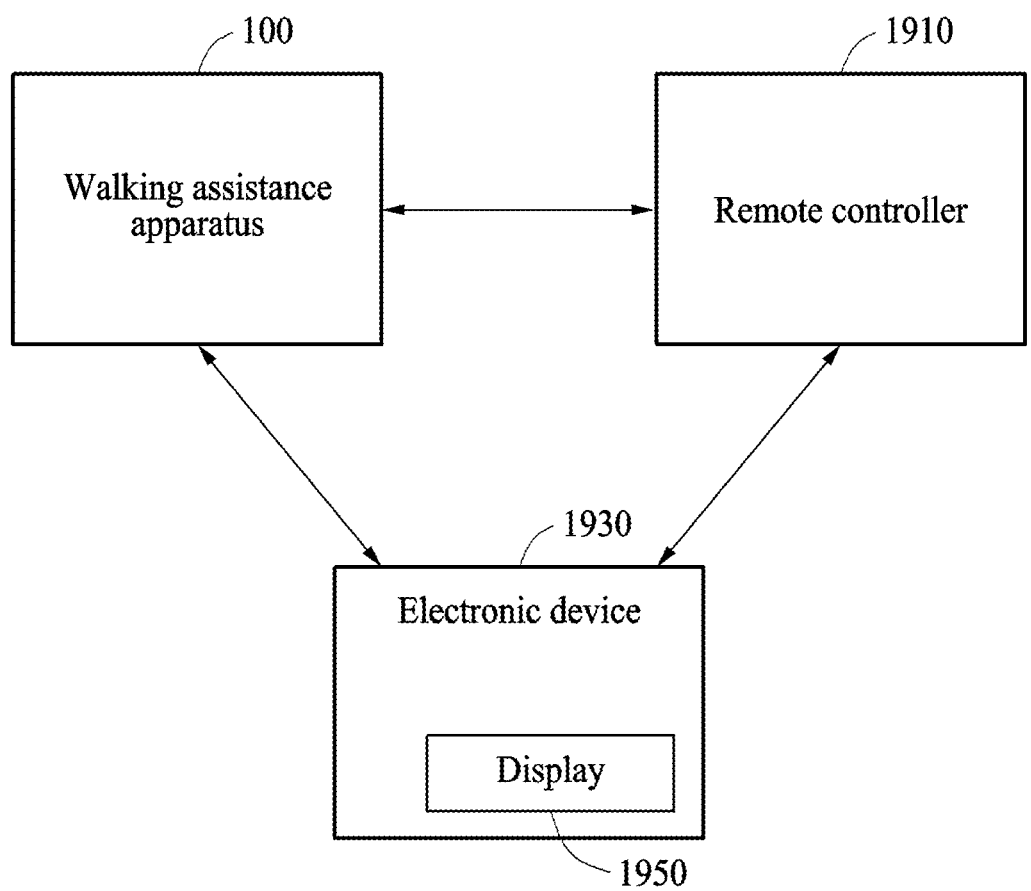
FIG. 20 is a block diagram illustrating still another example of a walking assistance system according to at least one example embodiment.

FIG. 20 is a block diagram illustrating a walking assistance system 1900 according to at least one example embodiment.

Referring to FIG. 20, the walking assistance system 1900 may include the walking assistance apparatus 100, a remote controller 1910, and an electronic device 1930.

A configuration and operation of the remote controller 1910 may be substantially the same as a configuration and operation of the remote controller 1810 of FIG. 19.

The electronic device 1930 may communicate with the walking assistance apparatus 100 and/or the remote controller 1910.

The electronic device 1930 may be implemented as, for example, a portable electronic device including a display 1950.

The portable electronic device may be implemented as, for example, a laptop computer, a mobile phone, a smartphone, a tablet personal computer (PC), a mobile Internet device (MID), a personal digital assistant (PDA), an enterprise digital assistant (EDA), a digital still camera, a digital video camera, a portable multimedia player (PMP), a personal navigation device or portable navigation device (PND), a handheld game console, an e-book, or a smart device. The smart device may be implemented as, for example, a smart watch or a smart band.

The electronic device 1930 may include a biosensor that senses a biosignal of a user, and may transmit the sensed biosignal to the walking assistance apparatus 100 and/or the remote controller 1910.

In other example embodiments, the walking assistance apparatus 100 may be included in a tremor control system. For example, the walking assistance apparatus 100 may be used as a handheld device to compensate for a hand tremor. The walking assistance apparatus 100 may be applicable to various handheld devices capable of interacting with users as well as a wearable exoskeleton robot.

In other example embodiments, the walking assistance apparatus 100 may be included in a vibration reduction system. For example, the walking assistance apparatus 100 may be utilized for a vibration reduction control of a surgical robot tool, a master device and/or a robotic slave device. The walking assistance apparatus 100 may employ a small number of sensors, and accordingly it is possible to reduce maintenance costs for calibration of the sensors by reducing a possibility of a malfunction and error of the sensors in various situations by a contact with a user. Also, it is possible to provide a degree of freedom in a design and usability by innovatively reducing a weight and volume of the walking assistance apparatus 100.

Figure 21:
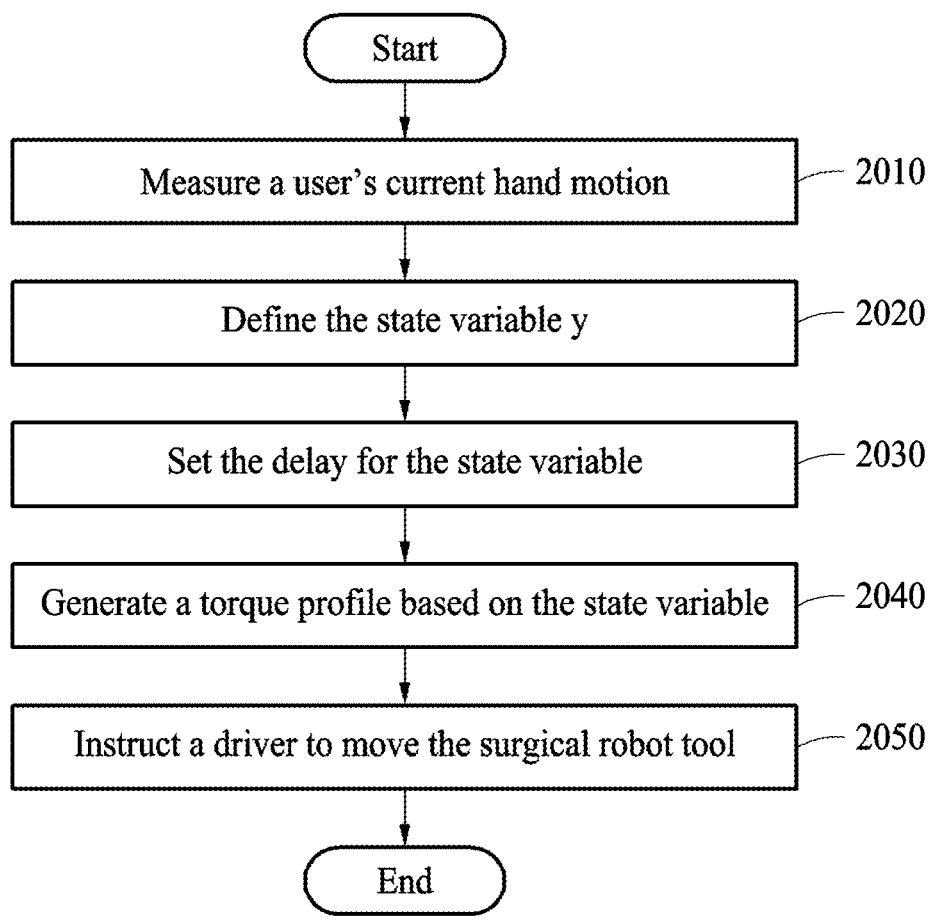
FIG. 21 illustrates a flowchart illustrating method of operating a walking assistance system for tremor control according to at least one example embodiment.

FIG. 21 illustrates a flowchart illustrating method of operating a walking assistance system for tremor control according to at least one example embodiment.

Referring to FIG. 21, in operation 2010, the controller 120 may measure a user's current hand motion. In operation 2020, the controller 120 may define the state variable y. In operation 2030, the controller 120 may set the delay for the state variable. In operation 2040, the controller 120 may generate a torque profile based on the state variable. In operation 2050, the controller 120 may instruct a driver to move the surgical robot tool such that surgical robot tool does not respond to tremors present in the measured hand motion.

Figure 22:
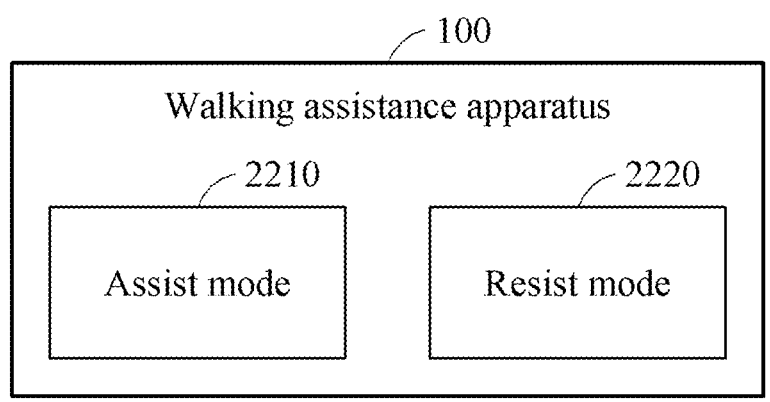
FIG. 22 is a diagram illustrating operating modes of the walking assistance apparatus of FIG. 1.

FIG. 22 is a diagram illustrating operating modes of the walking assistance apparatus 100 of FIG. 1.

The walking assistance apparatus 100 may filter motion information of a user. For example, the walking assistance apparatus 100 may measure a right hip joint angle and a left hip joint angle, and may perform low-pass filtering on a measurement result of the right hip joint angle and a measurement result of the left hip joint angle. Thus, a waveform of each of the measurement result of the right hip joint angle and the measurement result of the left hip joint angle may be smoothed. Also, an output of torque may be delayed due to filtering, as described above. In other words, a time delay due to the filtering may occur.

The walking assistance apparatus 100 may define a state variable based on the filtered motion information. For example, the walking assistance apparatus 100 may define a state variable y(t) corresponding to a difference between $\sin(q_r(t))$ and $\sin(q_l(t))$. In this example $q_r(t)$ denotes the filtered measurement result of the right hip joint angle, and $q_l(t)$ denotes the filtered measurement result of the left hip joint angle.

The walking assistance apparatus 100 may generate a torque profile based on a state variable, a gain and a delay. For example, a torque profile may be represented by Equation 9 shown below.

$$T(t) = Ay(t - \Delta t) \quad \text{[Equation 9]}$$

In Equation 9, T(t) denotes a torque profile, and A denotes a gain and may be a positive number or a negative number. For example, the gain A may be a positive gain or a negative gain. The gain A may correspond to an element that determines a strength and/or a direction (or a rotation direction) of torque, and may be adjusted by a user 200 or a manager. Also, y(t) in Equation 9 denotes a state variable. $\Delta t$ in Equation 9 denotes a delay and may correspond to an element that determines an output timing of torque. For example, $\Delta t$ may be a constant value in a range of 0.2 to 0.4. The above range of $\Delta t$ is merely an example, and a range of $\Delta t$ is not limited thereto.

Torque based on the torque profile may be output at a point in time delayed, by the time delay due to the filtering and the delay $\Delta t$, from a point in time at which the motion information is measured. For example, when the motion information is measured at a point in time t, the walking assistance apparatus 100 may output torque at a point in time "t+$t_{filter\ delay}$+$\Delta t$". In this example, $t_{filter\ delay}$ denotes the time delay due to the filtering.

Referring to FIG. 22, the walking assistance apparatus 100 may operate in an assist mode 2210, or a resist mode 2220. The walking assistance apparatus 100 may output torque to assist a gait motion (or a gait) of a user in the assist mode 2210, and may output torque to resist a gait motion (or a gait) of a user in the resist mode 2220.

In the assist mode 2210, the walking assistance apparatus 100 may generate a torque profile to assist a gait motion (or a gait) based on a state variable, a first gain and a delay. The first gain may be, for example, the above-described positive gain A. For example, the walking assistance apparatus 100 may generate a torque profile to assist a gait motion (or a gait) of a user by applying the positive gain A and the delay $\Delta t$ to the state variable y(t) based on Equation 9 described above.

The walking assistance apparatus 100 may output torque based on the generated torque profile. For example, the walking assistance apparatus 100 may output torque to assist a gait of a user based on a corresponding torque profile. Thus, the walking assistance apparatus 100 may assist the gait of the user.

In the resist mode 2220, the walking assistance apparatus 100 may generate a torque profile to provide a resistance to a gait motion (or a gait) based on a state variable, a second gain and a delay. The second gain may have a different sign from that of the first gain. The second gain may be the above-described negative gain A. For example, the walking assistance apparatus 100 may generate a torque profile to provide a resistance to a gait motion (or a gait) of a user by applying the negative gain A and the delay $\Delta t$ to the state variable y(t) based on Equation 9 described above.

The walking assistance apparatus 100 may output torque based on the torque profile to provide the resistance to the gait motion. For example, the walking assistance apparatus 100 may output torque to provide a resistance to a gait motion of a user based on a corresponding torque profile. Thus, the walking assistance apparatus 100 may enhance a leg strength of a user.

Figure 23:
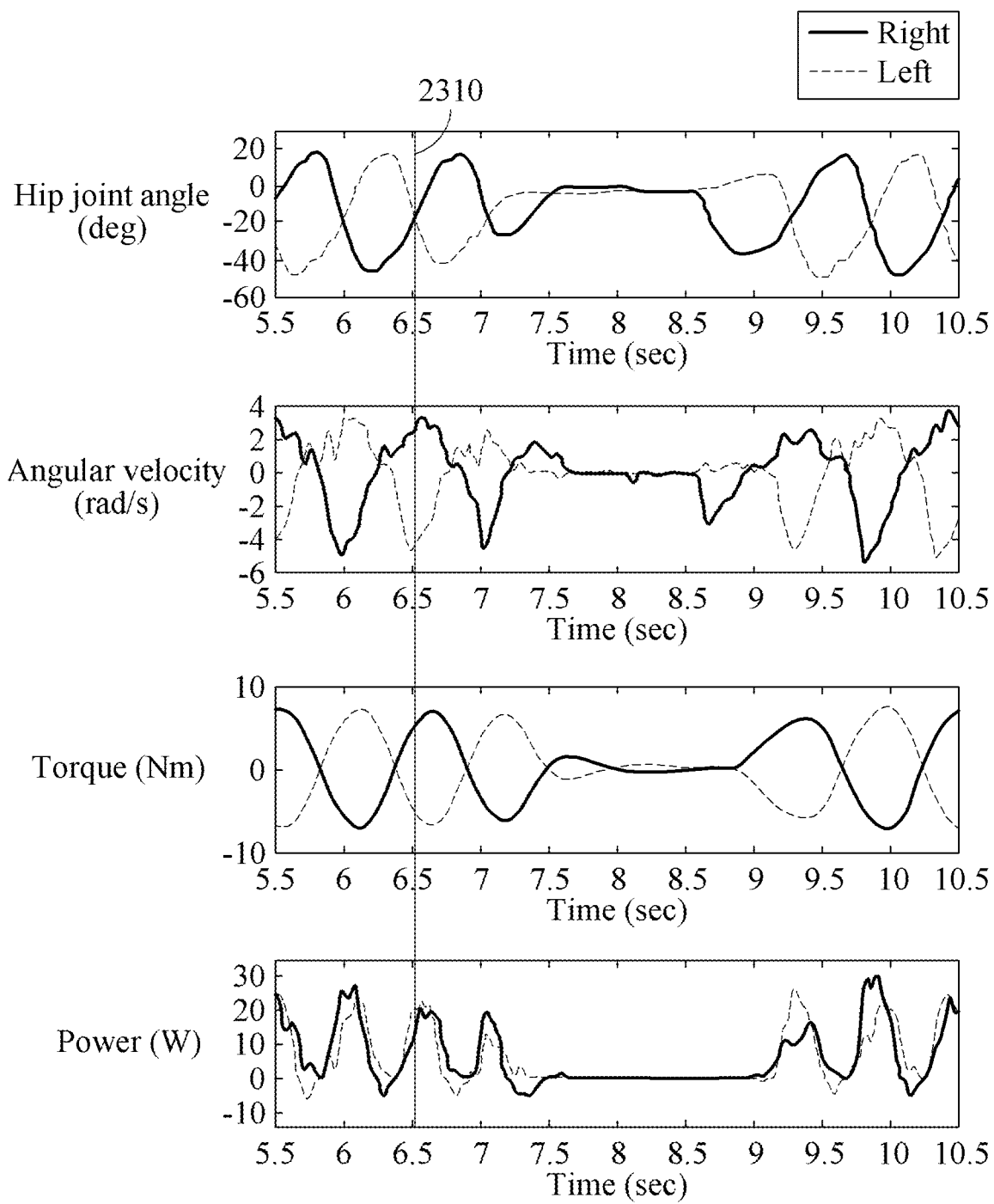
FIGS. 23 and 24 illustrate an assist mode of the walking assistance apparatus of FIG. 1.
Figure 24:
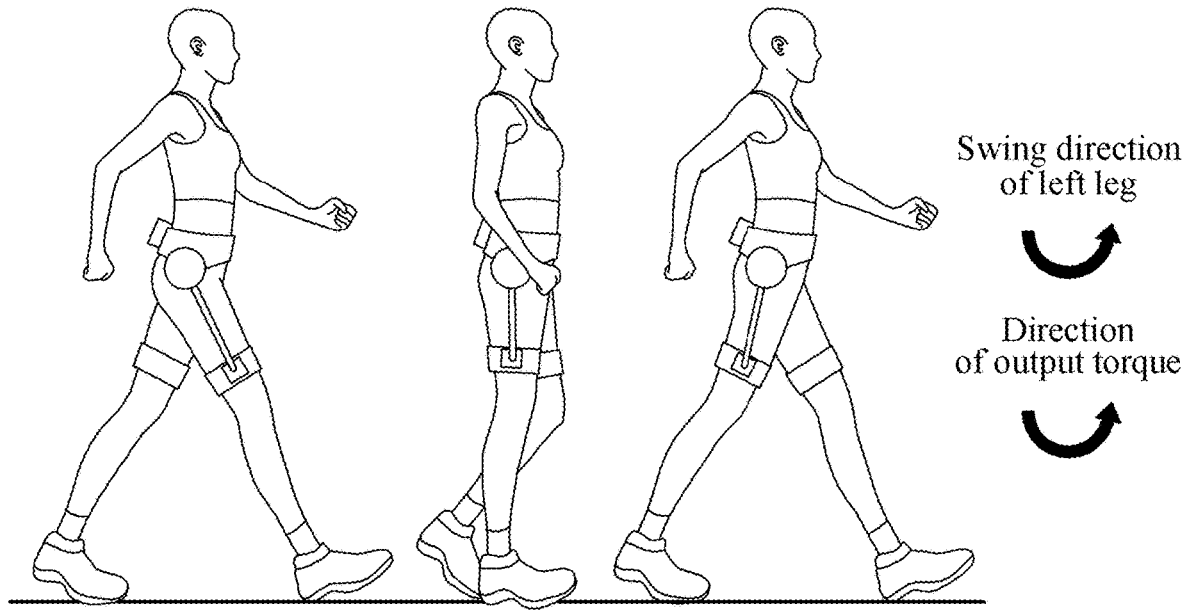

FIGS. 23 and 24 illustrate an assist mode of the walking assistance apparatus 100 of FIG. 1.

FIG. 23 illustrates an operation result of the walking assistance apparatus 100 when $\Delta t$ and A of Equation 9 are set to "0.25" and "10," respectively.

A first graph of FIG. 23 shows a result obtained by low-pass filtering of a measurement result of each of a right hip joint angle and a left hip joint angle in the assist mode 2210. The walking assistance apparatus 100 may perform low-pass filtering on a measurement result of each of the right hip joint angle and the left hip joint angle, to obtain a smooth graph free from noise as shown in the first graph of FIG. 23.

A second graph of FIG. 23 shows an angular velocity of a right hip joint angle and an angular velocity of a left hip joint angle in the assist mode 2210. A third graph of FIG. 23 shows torque output to each of a right leg and a left leg in the assist mode 2210. At a point 2310 of FIG. 23 at which the right hip joint angle and the left hip joint angle intersect, the angular velocity of the left hip joint angle shown in the second graph, and the torque output to the left leg shown in the third graph may have the same minus sign, which may indicate that the walking assistance apparatus 100 currently outputs torque to a left leg of a user in the same direction as a swing direction of the left leg. In other words, the swing direction of the left leg may be identical to a direction of the torque output to the left leg.

The third graph of FIG. 23 may have a smooth waveform, which may indicate that the walking assistance apparatus 100 currently applies assistance torque corresponding to the smooth waveform to a leg of the user. By the above-described low-pass filtering, the assistance torque corresponding to the smooth waveform may be applied to the leg of the user.

A fourth graph of FIG. 23 shows a result obtained by multiplying the second graph and the third graph of FIG. 23. In the fourth graph of FIG. 23, most values are positive. Thus, it may be found that the walking assistance apparatus 100 effectively assists a gait of a user by outputting torque in the same direction as a swing direction of a leg of the user while the user is ambulatory.

Figure 25:
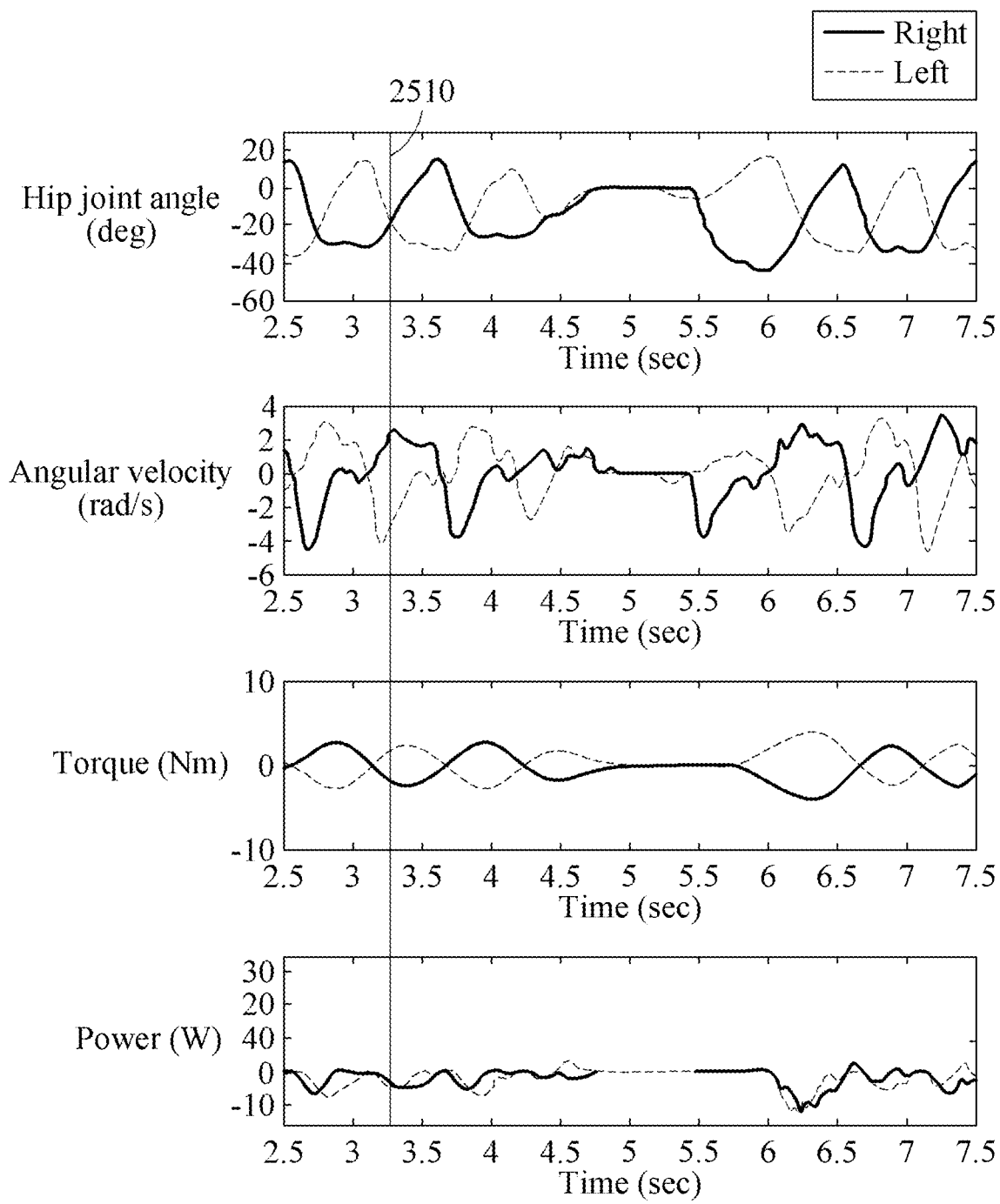
FIGS. 25 and 26 illustrate a resist mode of the walking assistance apparatus of FIG. 1.
Figure 26:
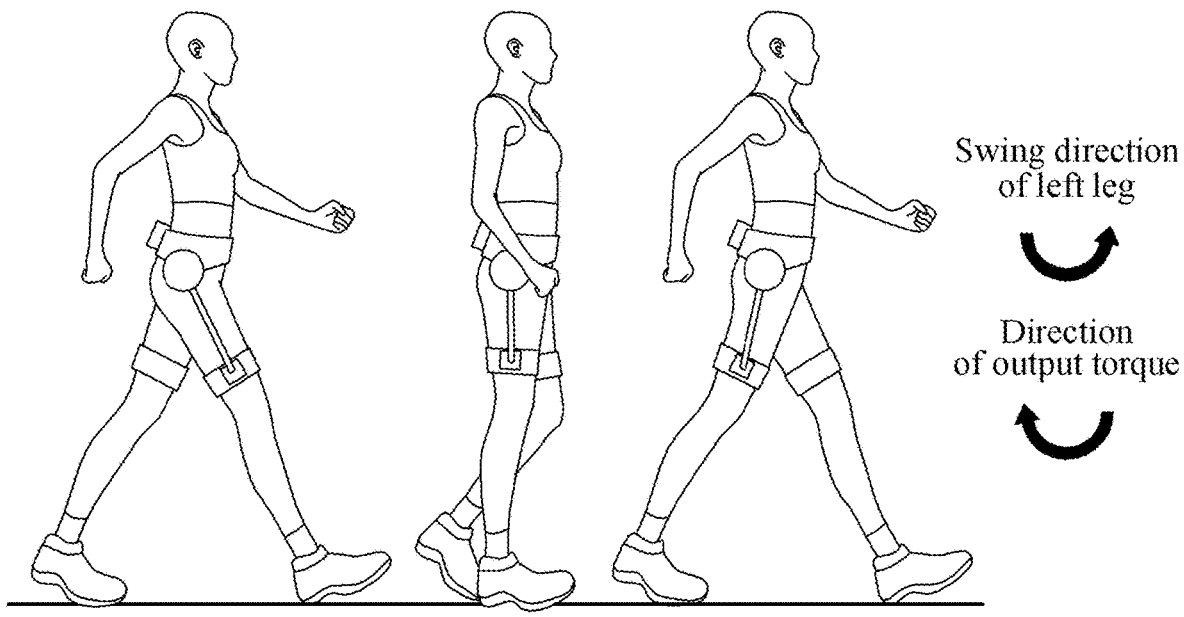

FIGS. 25 and 26 illustrate a resist mode of the walking assistance apparatus 100 of FIG. 1.

FIG. 25 illustrates an operation result of the walking assistance apparatus 100 when $\Delta t$ and A of Equation 9 are set to "0.25" and "−5," respectively.

A first graph of FIG. 25 shows a result obtained by low-pass filtering of a measurement result of each of a right hip joint angle and a left hip joint angle in the resist mode 2220. The walking assistance apparatus 100 may perform low-pass filtering on a measurement result of each of the right hip joint angle and the left hip joint angle, to obtain a smooth graph as shown in the first graph of FIG. 25.

A second graph of FIG. 25 shows an angular velocity of a right hip joint angle and an angular velocity of a left hip joint angle in the resist mode 2220. A third graph of FIG. 25 shows torque output to each of a right leg and a left leg in the resist mode 2220. At a point 2510 of FIG. 25 at which the right hip joint angle and the left hip joint angle intersect, the angular velocity of the left hip joint angle shown in the second graph may have a minus sign, and the torque output to the left leg shown in the third graph may have a plus sign. Thus, which may indicate that the walking assistance apparatus 100 currently outputs torque to a left leg of a user in the opposite direction as a swing direction of the left leg. Thus, the swing direction of the left leg may be different from a direction of the torque output to the left leg, as shown in FIG. 26.

The third graph of FIG. 25 may have a smooth waveform, which may indicate that the walking assistance apparatus 100 currently applies resistance torque corresponding to the smooth waveform to a leg of the user. By the above-described low-pass filtering, the resistance torque corresponding to the smooth waveform may be applied to the leg of the user.

A fourth graph of FIG. 25 shows a result obtained by multiplying angular velocities corresponding to the second graph of FIG. 25 and torque corresponding to the third graph of FIG. 25. In the fourth graph of FIG. 25, most values are negative, unlike the fourth graph of FIG. 23. Thus, it may be found that the walking assistance apparatus 100 effectively provides a resistance to a gait of a user.

Figure 27:
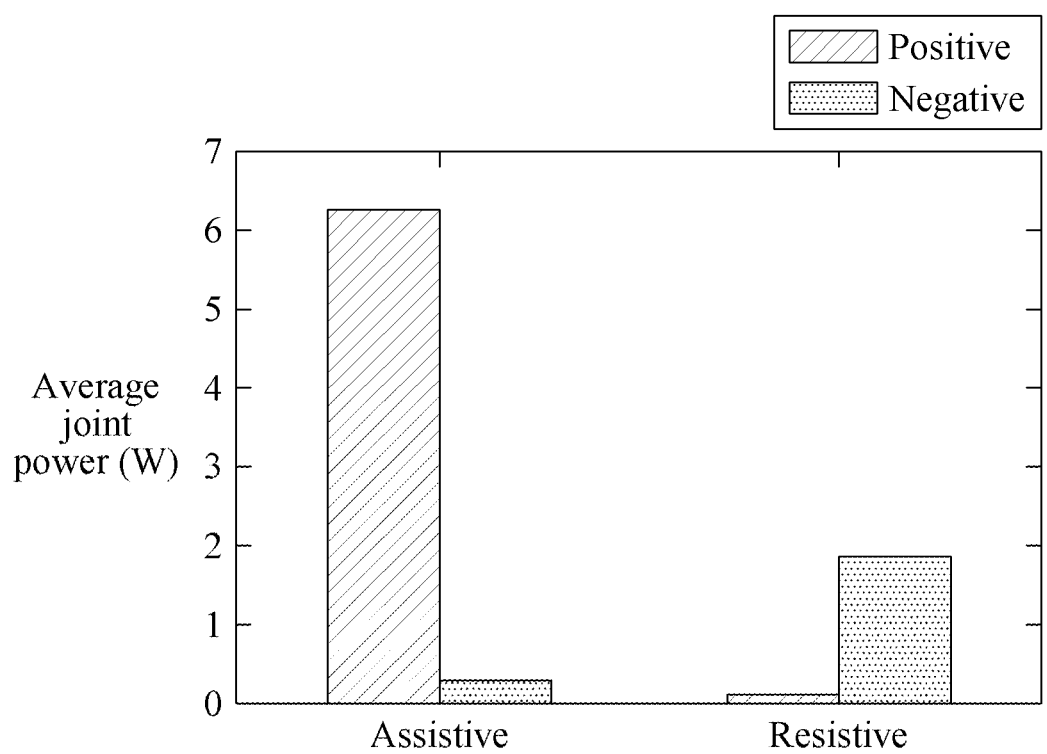
FIG. 27 is a graph illustrating a comparison between the assist mode and the resist mode of the walking assistance apparatus of FIG. 1.

FIG. 27 is a graph illustrating a comparison between an assist mode and a resist mode of the walking assistance apparatus 100 of FIG. 1.

In FIG. 27, "positive" means that a swing direction of a leg of a user is identical to a direction of torque output to the leg, and "negative" means that a swing direction of a leg of a user is different from a direction of torque output to the leg.

Also, "assistive" of FIG. 27 refers to an average of the fourth graph of FIG. 23 and is mostly occupied by "positive". Thus, it may be found that the walking assistance apparatus 100 efficiently assists a gait of a user by preventing the above-described mismatch.

In addition, "resistive" of FIG. 27 refers to an average of the fourth graph of FIG. 25 and is mostly occupied by "negative". In other words, the walking assistance apparatus 100 currently applies a resistance to a gait of a user. Thus, the walking assistance apparatus 100 may enhance a leg strength of the user.

Figure 28:
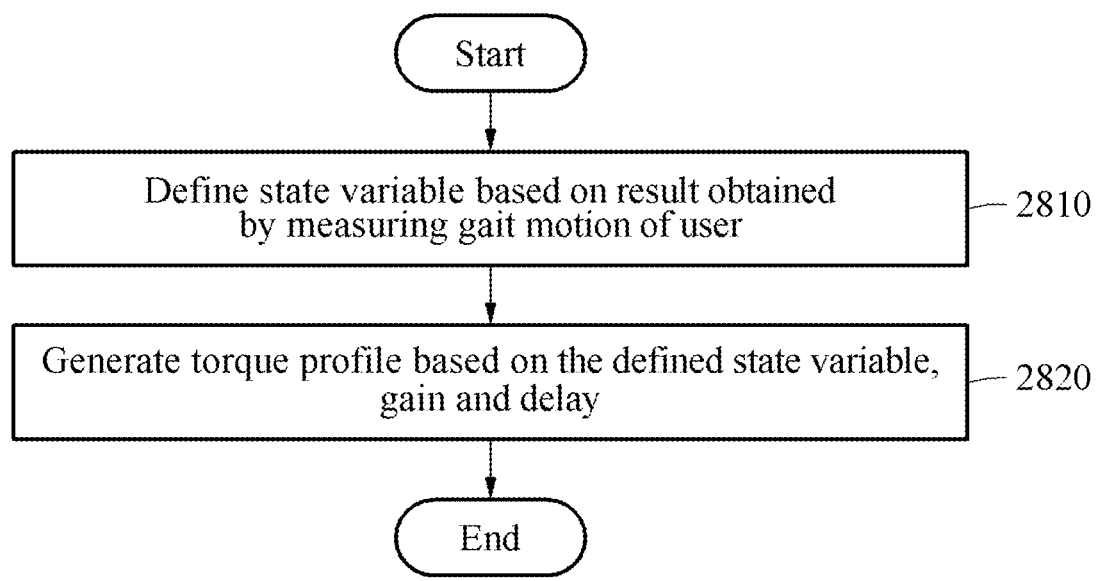
FIG. 28 is a flowchart illustrating an example of an operating method of the walking assistance apparatus of FIG. 1.

FIG. 28 is a flowchart illustrating an example of an operating method of the walking assistance apparatus 100 of FIG. 1.

Referring to FIG. 28, in operation 2810, the walking assistance apparatus 100 may define a state variable based on a result obtained by measuring a gait motion of a user. For example, the controller 120 of the walking assistance apparatus 100 may define the state variable based on the measured gait motion of the user.

In operation 2820, the walking assistance apparatus 100 may generate a torque profile based on the defined state variable, a gain and a delay. For example, the controller 120 of the walking assistance apparatus 100 may generate the torque profile using Equation 9 such that the torque profile is based on the defined state variable, the gain and the delay.

The generated torque profile may correspond to a torque profile to assist the gait motion, or a torque profile to provide a resistance to the gait motion.

For example, the walking assistance apparatus 100 may provide an assistance and a resistance step by step to a user's exercise (for example, a gait rehabilitation exercise). In other words, the walking assistance apparatus 100 may allow a user to perform an assistive exercise and a resistive exercise. Thus, a use range of the walking assistance apparatus 100 may be expanded.

The above description of FIGS. 1 through 27 may also be applicable to the operating method of FIG. 28, and accordingly is not repeated here.

Figure 29:
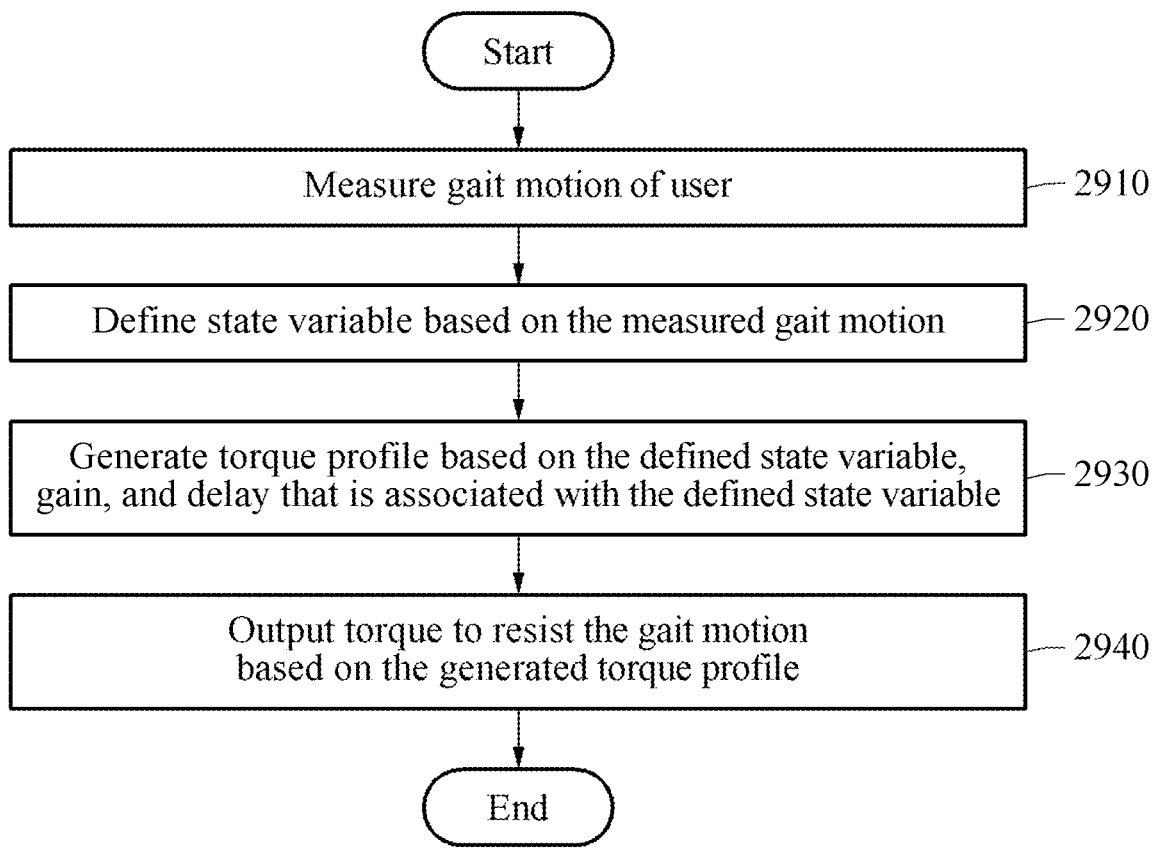
FIG. 29 is a flowchart illustrating another example of an operating method of the walking assistance apparatus of FIG. 1.

FIG. 29 is a flowchart illustrating another example of an operating method of the walking assistance apparatus 100 of FIG. 1.

The operating method of FIG. 29 may correspond to an operating method of the walking assistance apparatus 100 in the resist mode 2220.

Referring to FIG. 29, in operation 2910, the walking assistance apparatus 100 may measure a gait motion of a user. For example, as illustrated in FIG. 14, in operation 1310, the sensor 110 measure the left hip joint angle $q_l$, and, in operation 1320, the sensor 110 may measure the right hip joint angle $q_r$.

In operation 2920, the walking assistance apparatus 100 may define a state variable based on the measured gait motion. For example, the controller 120 of the walking assistance apparatus 100 may define the state variable y(t) based on a difference between $sin(q_r(t))$ and $sin(q_l(t))$, where $q_r(t)$ denotes the filtered measurement result of the right hip joint angle $q_r$, and $q_l(t)$ denotes the filtered measurement result of the left hip joint angle $q_l$.

In operation 2930, the walking assistance apparatus 100 may generate a torque profile based on the defined state variable, a gain and a delay. For example, the controller 120 of the walking assistance apparatus 100 may generate the torque profile using Equation 9 such that the torque profile is based on the defined state variable, the gain and the delay.

In operation 2940, the walking assistance apparatus 100 may output torque to resist the gait motion based on the generated torque profile. For example, the controller 120 of the walking assistance apparatus 100 may control the driver 230 based on the generated torque profile, and the driver 130 may output torque to resist the gait motion based on a control of the controller 120.

For example, the walking assistance apparatus 100 may provide a resistance step by step to a user's exercise by adjusting a gain within a negative range. Thus, the walking assistance apparatus 100 may allow the user to perform a resistive exercise, and accordingly it is possible to enhance an availability of the walking assistance apparatus 100.

The above description of FIGS. 1 through 27 may also be applicable to the operating method of FIG. 29, and accordingly is not repeated here.

The units and/or modules described herein may be implemented using hardware components, software components, or a combination thereof. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor.

Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An operating method of a walking assistance apparatus, the operating method comprising:
    operating the walking assistance apparatus in an assist mode when a gain associated with a torque rotation direction of the walking assistance apparatus is a first gain having a first sign and operating the walking assistance apparatus in a resist mode when the gain is a second gain having a second sign opposite to the first sign;
    measuring a first hip joint angle and a second hip joint angle of a user;
    determining a value of a state variable based on a difference between the first hip joint angle and the second hip joint angle;
    applying a delay that is used to delay a plurality of output timings of torque and the first gain to the value of the state variable when the walking assistance apparatus is in the assist mode and applying the delay and the second gain to the value of the state variable when the walking assistance apparatus is in the resist mode; and
    outputting assistance torque to the user by controlling a driver of the walking assistance apparatus based on a first torque profile when the walking assistance apparatus is in the assist mode and outputting resistance torque to the user by controlling the driver based on a second torque profile when the walking assistance apparatus is in the resist mode, wherein
    the first torque profile and the second torque profile indicate, for the plurality of output timings of torque, a value of the assistance torque and the resistance torque, respectively, at respective ones of the plurality of output timings of torque, and
    the first torque profile and the second torque profile are based on the value of the state variable at the respective ones of the plurality of output timings of torque shifted by the delay, the value of the state variable being amplified by the first gain for the first torque profile and the second gain for the second torque profile.

2. The operating method of claim 1, wherein the determining the value of the state variable comprises:
    determining the value of the state variable as a difference between a value of a first function based on the first hip joint angle of the user and a value of a second function based on the second hip joint angle.

3. The operating method of claim 2, wherein each of the first function and the second function corresponds to a trigonometrical function.

4. The operating method of claim 1, further comprising:
    filtering the first hip joint angle and the second hip joint angle.

5. The operating method of claim 4, wherein each of the plurality of output timings of torque is further delayed by a time delay associated with the filtering.

6. A walking assistance apparatus comprising:
    a sensor configured to measure a first hip joint angle and a second hip joint angle of a user;
    a driver configured to output an assistance torque or a resistance torque to the user; and
    a processor configured to,
        operate the walking assistance apparatus in an assist mode when a gain associated with a torque rotation direction of the walking assistance apparatus is a first gain having a first sign and operate the walking assistance apparatus in a resist mode when the gain is a second gain having a second sign opposite to the first sign,
        determine a value of a state variable based on a difference between the first hip joint angle and the second hip joint angle,
        apply a delay that is used to delay a plurality of output timings of torque and the first gain to the value of the state variable when the walking assistance apparatus is in the assist mode and apply the delay and the second gain to the value of the state variable when the walking assistance apparatus is in the resist mode, and
        control the driver based on a first torque profile such that the driver outputs the assistance torque when the walking assistance apparatus is in the assist mode and control the driver based on a second torque profile such that the driver outputs the resistance torque when the walking assistance apparatus is in the resist mode, wherein
        the first torque profile and the second torque profile indicate, for the plurality of output timings of torque, a value of the assistance torque and the resistance torque, respectively, at respective ones of the plurality of output timings of torque, and the first torque profile and the second torque profile are based on the value of the state variable at the respective ones of the plurality of output timings of torque shifted by the delay, the value of the state variable being amplified by the first gain for the first torque profile and the second gain for the second torque profile.

7. The walking assistance apparatus of claim 6, wherein the processor is configured to determine the value of the state variable as a difference between a value of a first function based on the first hip joint angle and a value of a second function based on the second hip joint angle.

8. The walking assistance apparatus of claim 7, wherein each of the first function and the second function corresponds to a trigonometrical function.

9. The walking assistance apparatus of claim 6, further comprising:

a filter configured to filter the first hip joint angle and the second hip joint angle.

10. The walking assistance apparatus of claim 9, wherein each of the plurality of output timings of torque is further delayed by a time delay associated with the filtering.

* * * * *